United States Patent
Van Nest et al.

(10) Patent No.: US 6,451,325 B1
(45) Date of Patent: *Sep. 17, 2002

(54) ADJUVANT FORMULATION COMPRISING A SUBMICRON OIL DROPLET EMULSION

(75) Inventors: Gary Van Nest, El Sorbrante; Gary Ott, Livermore; Gail Barchfeld, Alameda, all of CA (US)

(73) Assignee: Chiron Corporation, Emeryville, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 08/434,512

(22) Filed: May 4, 1995

Related U.S. Application Data

(60) Division of application No. 08/418,870, filed on Apr. 7, 1995, now Pat. No. 6,299,884, which is a continuation of application No. 08/215,007, filed on Mar. 21, 1994, now abandoned, which is a continuation of application No. 08/041,519, filed on Apr. 1, 1993, now abandoned, which is a continuation of application No. 07/885,905, filed on May 18, 1992, now abandoned, which is a continuation of application No. 07/528,593, filed on May 24, 1990, now abandoned, which is a continuation-in-part of application No. 07/357,035, filed on May 25, 1989, now abandoned.

(51) Int. Cl.$^7$ ............................................. A61K 39/39
(52) U.S. Cl. ........................... 424/283.1; 424/184.1; 424/450; 424/278.1; 514/8; 514/18; 514/2; 514/21; 514/970; 514/975
(58) Field of Search ................................ 424/450, 184.1, 424/278.1, 283.1; 514/8, 18, 2, 970, 975, 21

(56) References Cited

U.S. PATENT DOCUMENTS

| | | | | |
|---|---|---|---|---|
| 3,678,149 A | * | 7/1972 | Prigal | 424/8 |
| 3,790,665 A | * | 2/1974 | Glass et al. | 424/81 |
| 3,919,411 A | * | 11/1975 | Glass et al. | 424/81 |
| 4,613,505 A | * | 9/1986 | Mizushima et al. | 424/80 |
| 5,109,026 A | * | 4/1992 | Hoskinson et al. | 514/777 |
| 5,376,369 A | * | 12/1994 | Allison et al. | 424/88 |
| 5,709,879 A | * | 1/1998 | Barchfeld et al. | |
| 5,804,199 A | * | 9/1998 | Aasjord et al. | |
| 5,961,970 A | * | 10/1999 | Lowell et al. | |
| 6,086,901 A | * | 7/2000 | O'Hagan et al. | |

FOREIGN PATENT DOCUMENTS

| | | |
|---|---|---|
| EP | 0 135 376 | 3/1985 |
| EP | 0 315 153 A2 | 10/1989 |
| EP | 0 382 271 | 8/1990 |

OTHER PUBLICATIONS

Cox 1991 TIBTECH; November, vol. 9: 389–394.*
Hoffman et al 1987. Science 237:639–642.*
Sanchez–Pescador et al. 1988, The effect of adjuvants on the efficacy of a recombinant . . . , J. Immunol. 141(5):1720–1727.*
Haynes. 1993. Scientific and Social Issues of Human Immunodificiency . . . Science 260:1279–86.*
Fox 1994 BioTechnology. No Winners against AIDS vol. 12:128.*
Idson IN: Pharmaceutical Dosage Forms. vol. 1 Editor: Lieberman et al pp. 199–243, 1988.*
Remington's Pharmaceutical Sciences. Ed: Gennaro; pp. 298–299, 317–29, 1507–1511, 1985.*
Ott et al. Vaccine 13/16:1557–1562, 1995.*
Higgins et al. Vaccine 14/6:478–484, 1996.*
Stone et al, Avian Diseases, 22(4):666–674, 1978.*
Stone et al, Avian Diseases, 34:979–983, 1990.*
Decision of the Technical Board of Appeal 3.3.2 of Aug. 17, 2000.
The appeal of the Opposition Division's Decision to Revoke Regarding EP 399843 was dismissed and the patent was revoked.
Chiron Statement of Grounds for Appeal dated Dec. 30, 1997.
Affidavit of Lynn F Woodard dated Dec. 29, 1997.
Memorandum in Response to Chiron's Appeal of the Opposition Division's Decision to Revoke EP 399843.
Declaration of Dr. Anthony Allison.
Declaration of Dr. Kent R. Myers.
Declaration of Dr. J. Terry Ulrich.
Declaration of Patricia Momin.
Declaration of Dr. Michel Deschuyteneer.
Declaration of Dr. Georges Carletti.
Akzo Nobel Response dated Nov. 18, 1998.
Affidavit of John D. Barackman and Mastersizer Results.
Becher, *Emulsions Theory and Practice*, 2nd Edition, Chapter 5, (1965).
Herbert, "The Mode of Action of Mineral –Oil Emulsion Adjuvants on Antibody Production in Mice," *Immunology* 14:301–318 (1968).
Kaufman et al., "Spectral Absorption Measurements for Determination of Ease of Formation and Stability of Oil in Water Emulsions," *J. Dispersion Science and Technology* 2(4):475–480 (1981).
Ott et al., *Vaccine Design: The Subunit and Adjuvant Approach*, Chapter 10, Powell et al., Ed., Plenum Press, New York.
Sanchez–Pescador et al., "The Effect of Adjuvants on the Efficacy of a Recombinant Herpes Simplex Virus Glycoprotein Vaccine," *J. Immunology* 141:1720–1727 (1988).

(List continued on next page.)

*Primary Examiner*—Donna C. Wortman
*Assistant Examiner*—Robert A. Zeman
(74) *Attorney, Agent, or Firm*—Roberta L. Robins; Alisa A. Harbin; Robert P. Blackburn

(57) ABSTRACT

An adjuvant composition, comprising a metabolizable oil and an emulsifying agent, wherein the oil and the detergent are present in the form of an oil-in-water emulsion having oil droplets substantially all of which are less than 1 micron in diameter. In preferred embodiments, the emulsifying agent is also an immunostimulating agent, such as a lipophilic muramyl peptide. Alternatively, an immunostimulating agent separate from the emulsifying agent can be used.

49 Claims, No Drawings

OTHER PUBLICATIONS

Silvestri et al., "Theoretical Evaluation of Dispersed Droplet Radii in Submicron Oil–in–Water Emulsions," *International Journal of Pharmaceutics* 50(2):141–146 (1988).

Singh et al., "Parenteral Emulsions as Drug Carrier Systems," *J. Parenteral Science & Technology* 40(1):34–41 (1988).

Woodard et al., "Stable Oil–in–Water Emulsions; Preparation and Use as Vaccine Vehicles for Lipophllic Adjuvants." *Vaccine* 3:137–144 (1985).

Yarkoni et al., "Influence of Type of Oil and Surfactant Concentration on the Efficacy of Emulsified *Mycobacterium bovis* BCG Cell Walls to Induce Tumor Regression in Guinea Pigs," *Infection and Immunity* 28(3):881–886 (1980).

Copy of Decision Revoking the European Patent.

Statement of Grounds of Appeal to the Decision Revoking the European Patent.

* cited by examiner

ADJUVANT FORMULATION COMPRISING A SUBMICRON OIL DROPLET EMULSION

This application is a divisional of U.S. Ser. No. 08/418,870, filed Apr. 7, 1995, now U.S. Pat. No. 6,299,884; which was a continuation of U.S. Ser. No. 08/215,007, filed Mar. 21, 1994, now abandoned; which was a continuation of U.S. Ser. No. 08/041,519, filed Apr. 1, 1993, now abandoned; which was a continuation of U.S. Ser. No. 07/885,905, filed May 18, 1992, now abandoned; which was a continuation of U.S. Ser. No. 07/528,593, filed May 24, 1990, now abandoned; which was a continuation-in-part of U.S. Ser. No. 07/357,035, filed May 25, 1989, now abandoned; all of the foregoing are hereby incorporated by reference.

TECHNICAL FIELD

This invention relates generally to immunological adjuvants for use in increasing efficiency of vaccines and is particularly directed to adjuvants comprising oil-in-water emulsions.

BACKGROUND

The emergence of new subunit vaccines created by recombinant DNA technology has intensified the need for safe and effective adjuvants. Traditional live anti-viral vaccines require no adjuvants. Killed virus vaccines are generally much more immunogenic than subunit vaccines and can be effective with no adjuvant or with adjuvants that have limited ability to stimulate immune responses. The new, recombinant DNA-derived subunit vaccines, while offering significant advantages over the traditional vaccines in terms of safety and cost of production, generally represent isolated proteins or mixtures of proteins that have limited immunogenicity compared to whole viruses. Such materials are referred to generally in this specification as molecular antigens, to distinguish them from the whole organisms (and parts thereof) that were previously used in vaccines. These vaccines will require adjuvants with significant immunostimulatory capabilities to reach their full potential in preventing disease.

Currently, the only adjuvants approved for human use in the United States are aluminum salts (alum). These adjuvants have been useful for some vaccines including hepatitis B, diphtheria, polio, rabies and influenza, but may not be useful for others, especially if stimulation of cell-mediated immunity is required for protection. Reports indicate that alum failed to improve the effectiveness of whooping cough and typhoid vaccines and provided only a slight effect with adenovirus vaccines. Problems with aluminum salts include induction of granulomas at the injection site and lot-to-lot variation of alum preparations.

Complete Freund's adjuvant (CFA) is a powerful immunostimulatory agent that has been used successfully with many antigens on an experimental basis. CFA is comprised of three components: a mineral oil, an emulsifying agent such as Arlacel A, and killed mycobacteria such as *Mycobacterium tuberculosis*. Aqueous antigen solutions are mixed with these components to create a water-in-oil emulsion. CFA causes severe side effects, however, including pain, abscess formation, and fever, which prevent its use in either human or veterinary vaccines. The side effects are primarily due to the host's reactions to the mycobacterial component of CFA. Incomplete Freund's adjuvant (IFA) is similar to CFA without the bacterial component. While not approved for use in the United States, IFA has been useful for several types of vaccines in other countries. IFA has been used successfully in humans with influenza and polio vaccines and with several animal vaccines including rabies, canine distemper, and foot-and-mouth disease. Experiments have shown that both the oil and emulsifier used in IFA can cause tumors in mice, indicating that an alternative adjuvant would be a better choice for human use.

Muramyl dipeptide (MDP) represents the minimal unit of the mycobacterial cell wall complex that generates the adjuvant activity observed with CFA; see Ellouz et al. (1974) *Biochem. Biophys. Res. Comm.*, 59:1317. Many synthetic analogues of MDP have been generated that exhibit a wide range of adjuvant potency and side effects (reviewed in Chedid et al. (1978) *Prog. Allergy*, 25:63). Three analogues that may be especially useful as vaccine adjuvants are threonyl derivatives of MDP, see Byars et al. (1987) *Vaccine*, 5:223; n-butyl derivatives of MDP, see Chedid et al. (1982) *Infect. and Immun.*, 35:417; and lipophilic derivative of muramyl tripeptide, see Gisler et al. (1981) in *Immunomodulations of Microbial Products and Related Synthetic Compounds*, Y. Yamamura and S. Kotani, eds., Excerpta Medica, Amsterdam, p. 167. These compounds effectively stimulate humoral and cell-mediated immunity and exhibit low levels of toxicity.

One promising lipophilic derivative of MDP is N-acetylmuramyl-L-alanyl-D-isoglutaminyl-L-alanine-2-[1,2-dipalmitoyl-sn-glycero-3-3(hydroxyphosphoryloxy)]ethylamide (MTP-PE). This muramyl tripeptide has phospholipid tails that allow association of the hydrophobic portion of the molecule with a lipid environment while the muramyl peptide portion associates with the aqueous environment. Thus the MTP-PE itself can act as an emulsifying agent to generate stable oil in water emulsions.

Original mouse experiments in the laboratories of the present inventors with MTP-PE showed that this adjuvant was effective in stimulating anti-HSV gD antibody titers against herpes simplex virus gD antigen and that effectiveness was vastly improved if the MTP-PE and gD were delivered in oil (IFA) rather than in aqueous solution. Since IFA is not approved for human use, other oil delivery systems were investigated for MTP-PE and antigen. An emulsion of 4% squalene with 0.008% Tween 80 and HSV gD gave very good immunity in the guinea pig. This formulation, MTP-PE-LO (low oil), was emulsified by passing through a hypodermic needle and was quite unstable. Nevertheless, this formulation gave high antibody titers in the guinea pig and good protection in a HSV challenge of immunized guinea pigs. The formulation was most effective when delivered in the footpad but also gave reasonable antibody titers and protection when delivered intramuscularly. These data have appeared in.2 publications (Sanchez-Pescador et al., J. Immunology 141, 1720–1727, 1988 and Technological Advances in Vaccine Development, Lasky et al., ed., Alan R. Liss, Inc., p. 445–469, 1988). The MTP-PE-LO formulation was also effective in stimulating the immune response to the yeast-produced HIV envelope protein in guinea pigs. Both ELISA antibody titers and virus neutralizing antibody titers were stimulated to a high level with the MTP-PE formulation. However, when the same formulation was tested in large animals, such as goats and baboons, the compositions were not as effective. The desirability of additional adjuvant formulations for use with molecular antigens in humans and other large animals is evident.

SUMMARY OF THE INVENTION

Accordingly, it is an object of the present invention to provide an adjuvant formulation suitable for stimulating immune responses to molecular antigens in large mammals.

Surprisingly, it has been found that a satisfactory adjuvant formulation is provided by a composition comprising a metabolizable oil and an emulsifying agent, wherein the oil and the emulsifying agent are present in the form of an oil-in-water emulsion having oil droplets substantially all of which are less than 1 micron in diameter and wherein the composition exists in the absence of any polyoxyproplyene-polyoxyethylene block copolymer. Such block copolymers were previously thought to be essential for the preparation of submicron oil-in-water emulsions. The composition can also contain an immunostimulating agent (which can be the same as the emulsifying agent, if an amphipathic immunostimulating agent is selected).

DESCRIPTION OF SPECIFIC EMBODIMENTS

The present invention provides an adjuvant composition comprising a metabolizable oil and an emulsifying agent, wherein the oil and the emulsifying agent are present in the form of an oil-in-water emulsion having oil droplets substantially all of which are less than 1 micron in diameter. Investigations in the laboratories of the present inventors, reported in detail in the examples that follow, show a surprising superiority over adjuvant compositions containing oil and emulsifying agents in which the oil droplets are significantly larger than those provided by the present invention.

The individual components of the adjuvant compositions of the present invention are known, although such compositions have not been combined in the same manner and provided in a droplet size of such small diameter. Accordingly, the individual components, although described below both generally and in some detail for preferred embodiments, are well known in the art, and the terms used herein, such as metabolizable oil, emulsifying agent, immunostimulating agent, muramyl peptide, and lipophilic muramyl peptide, are sufficiently well known to describe these compounds to one skilled in the art without further description.

One component of these formulations is a metabolizable, non-toxic oil, preferably one of 6 to 30 carbon atoms including, but not limited to, alkanes, alkenes, alkynes, and their corresponding acids and alcohols, the ethers and esters thereof, and mixtures thereof. The oil may be any vegetable oil, fish oil, animal oil or synthetically prepared oil which can be metabolized by the body of the subject to which the adjuvant will be administered and which is not toxic to the subject. The subject is an animal, typically a mammal, and preferably a human. Mineral oil and similar toxic petroleum distillate oils are expressly excluded from this invention.

The oil component of this invention may be any long chain alkane, alkene or alkyne, or an acid or alcohol derivative thereof either as the free acid, its salt or an ester such as a mono-, or di- or triester, such as the triglycerides and esters of 1,2-propanediol or similar poly-hydroxy alcohols. Alcohols may be acylated employing a mono- or poly-functional acid, for example acetic acid, propanoic acid, citric acid or the like. Ethers derived from long chain alcohols which are oils and meet the other criteria set forth herein may also be used.

The individual alkane, alkene or alkyne moiety and its acid or alcohol derivatives will have 6–30 carbon atoms. The moiety may have a straight or branched chain structure. It may be fully saturated or have one or more double or triple bonds. Where mono or poly ester- or ether-based oils are employed, the limitation of 6–30 carbons applies to the individual fatty acid or fatty alcohol moieties, not the total carbon count.

Any metabolizable oil, particularly from an animal, fish or vegetable source, may be used herein. It is essential that the oil be metabolized by the host to which it is administered, otherwise the oil component may cause abscesses, granulomas or even carcinomas, or (when used in veterinary practice) may make the meat of vaccinated birds and animals unacceptable for human consumption due to the deleterious effect the unmetabolized oil may have on the consumer.

Sources for vegetable oils include nuts, seeds and grains. Peanut oil, soybean oil, coconut oil, and olive oil, the most commonly available, exemplify the nut oils. Seed oils include safflower oil, cottonseed oil, sunflower seed oil, sesame seed oil and the like. In the grain group, corn oil is the most readily available, but the oil of other cereal grains such as wheat, oats, rye, rice, teff, triticale and the like may also be used.

The technology for obtaining vegetable oils is well developed and well known. The compositions of these and other similar oils may be found in, for example, the Merck Index, and source materials on foods, nutrition and food technology.

The 6–10 carbon fatty acid esters of glycerol and 1,2-propanediol, while not occurring naturally in seed oils, may be prepared by hydrolysis, separation and esterification of the appropriate materials starting from the nut and seed oils. These products are commercially available under the name NEOBEE® from PVO International, Inc., Chemical Specialties Division, 416 Division Street, Boongon, N.J. and others.

Oils from any animal source, may be employed in the adjuvants and vaccines of this invention. Animal oils and fats are usually solids at physiological temperatures due to the fact that they exist as triglycerides and have a higher degree of saturation than oils from fish or vegetables. However, fatty acids are obtainable from animal fats by partial or complete triglyceride saponification which provides the free fatty acids. Fats and oils from mammalian milk are metabolizable and may therefore be used in the practice of this invention. The procedures for separation, purification, saponification and other means necessary for obtaining pure oils from animal sources are well known in the art.

Most fish contain metabolizable oils which may be readily recovered. For example, cod liver oil, shark liver oils, and whale oil such as spermaceti exemplify several of the fish oils which may be used herein. A number of branched chain oils are synthesized biochemically in 5-carbon isoprene units and are generally referred to as terpenoids. Shark liver oil contains a branched, unsaturated terpenoids known as squalene, 2,6,10,15,19,23-hexamethyl-2,6,10,14,18,22-tetracosahexaene which is particularly preferred herein. Squalane, the saturated analog to squalene, is also a particularly preferred oil. Fish oils, including squalene and squalane, are readily available from commercial sources or may be obtained by methods known in the art.

The oil component of these adjuvants and vaccine formulations will be present in an amount from 0.5% to 20% by volume but preferably no more than 15%, especially in an amount of 1% to 12%. It is most preferred to use from 1% to 4% oil.

The aqueous portion of these adjuvant compositions is buffered saline or, in preferred embodiments, unadulterated water. Because these compositions are intended for parenteral administration, it is preferable to make up final buffered solutions used as vaccines so that the tonicity, i.e., osmolality, is essentially the same as normal physiological fluids in order to prevent post-administration swelling or rapid absorption of the composition because of differential ion concentrations between the composition and physiological fluids. It is also preferable to buffer the saline in order to maintain a pH compatible with normal physiological conditions. Also, in certain instances, it may be necessary to maintain the pH at a particular level in order to insure the stability of certain composition components such as the glycopeptides.

Any physiologically acceptable buffer may be used herein, but phosphate buffers are preferred. Other acceptable buffers such as acetate, tris, bicarbonate, carbonate, or the like may be used as substitutes for phosphate buffers. The pH of the aqueous component will preferably be between 6.0–8.0.

However, when the adjuvant is initially prepared, unadulterated water is preferred as the aqueous component of the emulsion. Increasing the salt concentration makes it more difficult to achieve the desired small droplet size. When the final vaccine formulation is prepared from the adjuvant, the antigenic material can be added in a buffer at an appropriate osmolality to provide the desired vaccine composition.

The quantity of the aqueous component employed in these compositions will be that amount necessary to bring the value of the composition to unity. That is, a quantity of aqueous component sufficient to make 100% will be mixed, with the other components listed above in order to bring the compositions to volume.

A substantial number of emulsifying and suspending agents are generally used in the pharmaceutical sciences. These include naturally derived materials such as gums from trees, vegetable protein, sugar-based polymers such as alginates and cellulose, and the like. Certain oxypolymers or polymers having a hydroxide or other hydrophilic substituent on the carbon backbone have surfactant activity, for example, povidone, polyvinyl alcohol, and glycol ether-based mono- and poly-functional compounds. Long chain fatty-acid-derived compounds form a third substantial group of emulsifying and suspending agents which could be used in this invention. Any of the foregoing surfactants are useful so long as they are non-toxic.

Specific examples of suitable emulsifying agents (also referred to as surfactants or detergents) which can be used in accordance with the present invention include the following:

1. Water-soluble soaps, such as the sodium, potassium, ammonium and alkanol-ammonium salts of higher fatty acids ($C_{10}$–$C_{22}$), and, particularly sodium and potassium tallow and coconut soaps.
2. Anionic synthetic non-soap detergents, which can be represented by the water-soluble salts of organic sulfuric acid reaction products having in their molecular structure an alkyl radical containing from about 8 to 22 carbon atoms and a radical selected from the group consisting of sulfonic acid and sulfuric acid ester radicals. Examples of these are the sodium or potassium alkyl sulfates, derived from tallow or coconut oil; sodium or potassium alkyl benzene sulfonates; sodium alkyl glyceryl ether sulfonates; sodium coconut oil fatty acid monoglyceride sulfonates and sulfates; sodium or potassium salts of sulfuric acid esters of the reaction product of one mole of a higher fatty alcohol and about 1 to 6 moles of ethylene oxide; sodium or potassium alkyl phenol ethylene oxide ether sulfonates, with 1 to 10 units of ethylene oxide per molecule and in which the alkyl radicals contain from 8 to 12 carbon atoms; the reaction product of fatty acids esterified with isethionic acid and neutralized with sodium hydroxide; sodium or potassium salts of fatty acid amide of a methyl tauride; and sodium and potassium salts of $SO_3$-sulfonated $C_{10}$–$C_{24}$ α-olefins.
3. Nonionic synthetic detergents made by the condensation of alkylene oxide groups with an organic hydrophobic compound. Typical hydrophobic groups include condensation products of propylene oxide with propylene glycol, alkyl phenols, condensation product of propylene oxide and ethylene diamine, aliphatic alcohols having 8 to 22 carbon atoms, and amides of fatty acids.
4. Nonionic detergents, such as amine oxides, phosphine oxides and sulfoxides, having semipolar characteristics. Specific examples of long chain tertiary amine oxides include dimethyldodecylamine oxide and bis-(2-hydroxyethyl) dodecylamine. Specific examples of phosphine oxides are found in U.S. Pat. No. 3,304,263 which issued Feb. 14, 1967, and include dimethyldodecyl-phosphine oxide and dimethyl-(2hydroxydodecyl) phosphine oxide.
5. Long chain sulfoxides, including those corresponding to the formula $R^1$—SO—$R^2$ wherein $R^1$ and $R^2$ are substituted or unsubstituted alkyl radicals, the former containing from about 10 to about 28 carbon atoms, whereas $R^2$ contains from 1 to 3 carbon atoms. Specific examples of these sulfoxides include dodecyl methyl sulfoxide and 3-hydroxy tridecyl methyl sulfoxide.
6. Ampholytic synthetic detergents, such as sodium 3-dodecylaminopropionate and sodium 3-dodecylaminopropane sulfonate.
7. Zwitterionic synthetic detergents, such as 3-(N,N-dimethyl-N-hexadecylammonio) propane-1-sulfonate and 3-(N,N-dimethyl-N-hexadecylammonio)-2-hydroxy propane-1-sulfonate.

Additionally, all of the following types of emulsifying agents can be used in a composition of the present invention: (a) soaps (i.e., alkali salts) of fatty acids, rosin acids, and tall oil; (b) alkyl arene sulfonates; (c) alkyl sulfates, including surfactants with both branched-chain and straight-chain hydrophobic groups, as well as primary and secondary sulfate groups; (d) sulfates and sulfonates containing an intermediate linkage between the hydrophobic and hydrophilic groups, such as the fatty acylated methyl taurides and the sulfated fatty monoglycerides; (e) long-chain acid esters of polyethylene glycol, especially the tall oil esters; (f) polyethylene glycol ethers of alkylphenols; (g) polyethylene glycol ethers of long-chain alcohols and mercaptans; and (h) fatty acyl diethanol amides. Since surfactants can be classified in more than one manner, a number of classes of surfactants set forth in this paragraph overlap with previously described surfactant classes.

There are a number of emulsifying agents specifically designed for and commonly used in biological situations. For example, a number of biological detergents (surfactants) are listed as such by Sigma Chemical Company on pages 310–316 of its 1987 Catalog of Biochemical and Organic Compounds. Such surfactants are divided into four basic types: anionic, cationic, zwitterionic, and nonionic. Examples of anionic detergents include alginic acid, caprylic acid, cholic acid, 1-decanesulfonic acid, deoxycholic acid, 1-dodecanesulfonic acid, N-lauroylsarcosine, and taurocholic acid. Cationic detergents include dodecyltrimethylammonium bromide, benzalkonium chloride, benzyldimethylhexadecyl ammonium chloride, cetylpyridinium chloride, methylbenzethonium chloride, and 4-picoline dodecyl sulfate. Examples of zwitterionic detergents include 3-[(3-cholamidopropyl)-dimethylammonio]-1-propanesulfonate (commonly abbreviated CHAPS), 3-[(cholamidopropyl)-dimethylammonio]-2-hydroxy-1-propanesulfonate (generally abbreviated CHAPSO), N-dodecyl-N,N-dimethyl-3-ammonio-1-propanesulfonate, and lyso-α-phosphatidylcholine. Examples of nonionic detergents include decanoyl-N-methylglucamide, diethylene glycol monopentyl-ether, n-dodecyl β-D-glucopyranoside, ethylene oxide condensates of fatty alcohols (e.g., sold under the trade name Lubrol), polyoxyethylene ethers of fatty acids (particularly $C_{12}$–$C_{20}$ fatty acids), polyoxyethylene sorbitan fatty acid ethers (e.g., sold under the trade name Tween), and sorbitan fatty acid ethers (e.g., sold under the trade name Span).

A particularly useful group of surfactants are the sorbitan-based non-ionic surfactants. These surfactants are prepared by dehydration of sorbitol to give 1,4-sorbitan which is then reacted with one or more equivalents of a fatty acid. The fatty-acid-substituted moiety may be further reacted with ethylene oxide to give a second group of surfactants.

The fatty-acid-substituted sorbitan surfactants are made by reacting 1,4-sorbitan with a fatty acid such as lauric acid, palmitic acid, stearic acid, oleic acid, or a similar long chain fatty acid to give the 1,4-sorbitan mono-ester, 1,g-sorbitan sesquiester or 1,4-sorbitan triester. The common names for these surfactants include, for example, sorbitan monolaurate, sorbitan monopalmitate, sorbitan monoestearate, sorbitan monooleate, sorbitan sesquioleate, and sorbitan trioleate. These surfactants are commercially available under the name "SPAN" or "ARLACEL", usually with a letter or number designation which distinguishes between the various mono, di- and triester substituted sorbitans.

"SPAN" and "ARLACEL" surfactants are hydrophilic and are generally soluble or dispersible in oil. They are also soluble in most organic solvents. In water they are generally insoluble but dispersible. Generally these surfactants will have a hydrophilic-lipophilic balance (HLB) number between 1.8 to 8.6. Such surfactants can be readily made by means known in the art or are commercially available from, for example, ICI America's Inc., Wilmington, Del. under the registered mark "ATLAS".

A related group of surfactants comprises polyoxyethylene sorbitan monoesters and polyoxyethylene sorbitan triesters. These materials are prepared by addition of ethylene oxide to a 1,4-sorbitan monester or triester. The addition of polyoxyethylene converts the lipophilic sorbitan mono- or tri-ester surfactant to a hydrophilic surfactant generally soluble or dispersible in water and soluble to varying degrees in organic liquids.

These materials, commercially available under the mark "TWEEN", are useful for preparing oil-in-water emulsions and dispersions, or for the solubilization of oils and making anhydrous ointments water-soluble or washable. The "TWEEN" surfactants may be combined with a related sorbitan monester or triester surfactants to promote emulsion stability. "TWEEN" surfactants generally have a HLB value falling between 9.6 to 16.7. "TWEEN" surfactants are commercially available from a number of manufacturers, for example ICI America's Inc., Wilmington, Del. under the registered mark "ATLAS" surfactants.

A third group of non-ionic surfactants which could be used alone or in conjunction with "SPAN", "ARLACEL" and "TWEEN" surfactants are the polyoxyethylene fatty acids made by the reaction of ethylene oxide with a long-chain fatty acid. The most commonly available surfactant of this type is solid under the name "MYRJ" and is a polyoxyethylene derivative of stearic acid. "MYRJ" surfactants are hydrophilic and soluble or dispersible in water like "TWEEN" surfactants. The MYRJ® surfactants may be blended with "TWEEN" surfactants or with TWEEN®/SPAN® or "ARLACEL" surfactant mixtures for use in forming emulsions. "MYRJ" surfactants can be made by methods known in the art or are available commercially from ICI America's Inc.

A fourth group of polyoxyethylene based non-ionic surfactants are the polyoxyethylene fatty acid ethers derived from lauryl, acetyl, stearyl and oleyl alcohols. These materials are prepared as above by addition of ethylene oxide to a fatty alcohol. The commercial name for these surfactants is BRIJ®. BRIJ® surfactants may be hydrophilic or lipophilic depending on the size of the polyoxyethylene moiety in the surfactant. While the preparation of these compounds is available from the art, they are also readily available from such commercial sources as ICI America's Inc.

Other non-ionic surfactants which could potentially be used in the practice of this invention are for example: polyoxyethylene, polyol fatty acid esters, polyoxyethylene ether, polyoxypropylene fatty ethers, bee's wax derivatives containing polyoxyethylene, polyoxyethylene lanolin derivative, polyoxyethylen fatty glycerides, glycerol fatty acid esters or other polyoxyethylene acid alcohol or ether derivatives of long-chain fatty acids of 12–22 carbon atoms.

As the adjuvant and the vaccine formulations of this invention are intended to be multi-phase systems, it is preferable to choose an emulsion-forming non-ionic surfactant which has an HLB value in the range of about 7 to 16. This value may be obtained through the use of a single non-ionic surfactant such as a TWEEN® surfactant or may be achieved by the use of a blend of surfactants such as with a sorbitan mono, di- or triester based surfactant; a sorbitan ester polyoxyethylene fatty acid; a sorbitan ester in combination with a polyoxyethylene lanolin derived surfactant; a sorbitan ester surfactant in combination with a high HLB polyoxyethylene fatty ether surfactant; or a polyethylene fatty ether surfactant or polyoxyethylene sorbitan fatty acid.

It is more preferred to use a single non-ionic surfactant, most particularly a "TWEEN" surfactant, as the emulsion stabilizing non-ionic surfactant in the practice of this invention. The surfactant named "TWEEN", otherwise known as polysorbate 80 for polyoxyethlyene 20 sorbitan monooleate, is the most preferred of the foregoing surfactants.

Sufficient droplet size reduction can usually be effected by having the surfactant present in an amount of 0.02% to 2.5% by weight (w/w). An amount of 0.05% to 1% is preferred with 0.01 to 0.5% being especially preferred.

The manner in which the droplet size of the invention is reached is not important to the practice of the present invention. One manner in which submicron oil droplets can be obtained is by use of a commercial emulsifiers, such as model number 110Y available from Microfluidics, Newton, Mass. Examples of other commercial emulsifiers include Gaulin Model 30CD (Gaulin, Inc., Everett, Mass.) and Rainnie Minilab Type 8.30 H (Miro Atomizer Food and Dairy, Inc., Hudson, Wis.). These emulsifiers operate by the principle of high shear forces developed by forcing fluids through small apertures under high pressure. When the model 110Y is operated at 5,000–30,000 psi, oil droplets having diameters of 100–750 nm are provided.

The size of the oil droplets can be varied by changing the ratio of detergent to oil (increasing the ratio decreases droplet size), operating pressure (increasing operating pressure reduces droplet size), temperature (increasing temperature decreases droplet size), and adding an amphipathic immunostimulating agent (adding such agents decreases droplet size). Actual droplet size will vary with the particular detergent, oil, and immunostimulating agent (if any) and with-the particular operating conditions selected. Droplet size can be verified by use of sizing instruments, such as the commercial Sub-Micron Particle Analyzer (Model N4MD) manufactured by the Coulter Corporation, and the parameters can be varied using the guidelines set forth above until substantially all droplets are less than 1 micron in diameter, preferably less than 0.8 microns in diameter, and most preferably less than 0.5 microns in diameter. By substantially all is meant at least 80% (by number), preferably at least 90%, more preferably at least 95%, and most preferably at least 98%. The particle size distribution is typically Gaussian, so that the average diameter is smaller than the stated limits.

The present invention is practiced by preparing an oil emulsion in the absence of other components previously taught in the prior art to be used with submicron emulsions for satisfactory immunogenicity, namely polyoxypropylene-polyoxyethlyne block polymers such as those described for use with adjuvants in U.S. Pat. Nos. 4,772,466 and 4,770,874 and in European Patent Application 0 315 153 A2.

An adjuvant composition of the invention consists essentially of a metabolizable oil in water and an emulsifying agent other than than a POP-POE copolymer. The emulsifying agent need not have any specific immunostimulating activity, since the oil composition by itself can function as an adjuvant when the oil droplets are in the submicron range. However, increased immunostimulating activity can be provided by including any of the known immunostimulating agents in the composition. These immunostimulating agents can either be separate from the emulsifying agent and the oil or the immunostimulating agent and the emulsifying agent can be one and the same molecule. Examples of the former situation include metabolizable oils mixed with killed mycobacteria, such as *Mycobacterium tuberculosis,* and subcellular components thereof. Additional immunostimulating substances include the muramyl peptides that are components of the cell walls of such bacteria. A number of preferred muramyl peptides are listed below. Examples of the joint emulsifying agent/immunostimulating agent are the lipophilic muramyl peptides described in the two Sanchez-Pescador et al. publications cited above. These materials comprise the basic N-acetylmuramyl peptide (a hydrophilic moiety) that acts as an immunostimulating group, but also include a lipophilic moiety that provides surface-active characteristics to the resulting compound. Such compounds, as well as other types of amphipathic immunostimulating substances, act as both immunostimulating agents and emulsifying agents and are preferred in the practice of the present invention. In addition, it is also possible to practice the present invention by using a amphiphatic immunostimulating substance in combination with a second immunostimulating substance that is not amphipathic. An example would be use of a lipophilic muramyl peptide in combination with an essentially unsubstituted (i.e., essentially hydrophilic) muramyl dipeptide.

The preferred immune-response-stimulating muramyl peptides (or more accurately glycopeptides) of this invention are a group of compounds related to and generally derived from N-acetylmuramyl-L-alanyl-D-isoglutamine, which was determined by Ellouz et al. (1974) *Biochem. & Biophys. Res. Comm.,* 59(4): 1317, to be the smallest effective unit possessing immunological adjuvant activity in *M. tuberculosis,* the mycobacterial component of Freund's complete adjuvant. A number of dipeptide- and polypeptide-substituted muramic acid derivatives were subsequently developed and found to have immunostimulating activity.

Though these glycopeptides are a diverse group of compounds, they can be generally represented by Formula I below:

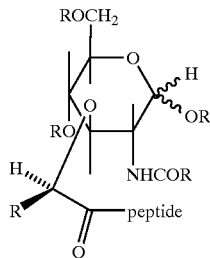

wherein the pyran ring oxygens are substituted by hydrogen, alkyl, or acyl or the like, or may be replaced by nitrogen-based substituents, particularly the 6-position oxygen; the 2-amino group is an acyl group or some other amide; the lactyl side chain is modified, e.g., is ethyl or another two-position alkyl moiety; and the peptide function is a dipeptide or polypeptide, which may be further derivatized. Furanosyl analogues of the pyranosyl compounds also have immunopotentiating activity and are useful in this invention.

Among the glycopeptides of this invention are those disaccharides and tetrasaccharides linked by meso-α,ε-diaminopimelic acid such as described in U.S. Pat. Nos. 4,235,771 and 4,186,194.

Immune response stimulating glycopeptides which may be used in the practice of this invention are disclosed in U.S. Pat. Nos. 4,094,971; 4,101,536; 4,153,684; 4,235,771; 4,323,559; 4,327,085; 4,185,089; 4,082,736; 4,369,178; 4,314,998 and 4,082,735; and 4,186,194. The glycopeptides disclosed in these patents are incorporated herein by reference and made a part hereof as if set out in full herein. The compounds of Japanese patent application Nos. JP 40792227, JP 4079228, and JP 41206696 would also be useful in the practice of this invention.

Methods for preparing these compounds are disclosed and well-known in the art. Preparative process exemplification can be found in U.S. Pat. Nos. 4,082,736 and 4,082,735. Additionally, similar preparative processes may be found in the U.S. patents referenced in the preceding paragraph.

Preferred glycopeptides are those having the Formula II

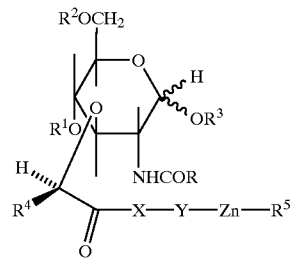

wherein

R is an unsubstituted or substituted alkyl radical containing from 1 to 22 carbon atoms, or an unsubstituted or substituted aryl radical containing from 6 to 10 carbon atoms;

$R^1$ and $R^2$ are the same or different and are hydrogen or an acyl radical containing from 1 to 22 carbon atoms;

$R^3$ is hydrogen, alkyl of 1 to 22 carbons, or aryl of 7 to 10 carbon atoms;

R is hydrogen or alkyl;

n is 0 or 1;

X and Z are independently alanyl, valyl, leucyl, isoleucyl, α-aminobutyryl, threonyl, methionyl, cysteinyl, glutamyl, glutaminyl, isoglutamyl, isoglutaminyl, aspartyl, phenylalanyl, tyrosyl, lysyl, ornithinyl, arginyl, histidyl, asparaginyl, prolyl, hydroxyprolyl, seryl, or glycyl;

$R^5$ is an optionally esterified or amidated carboxyl group of the terminal amino acid; and Y is —NHCHR$^6$CH$_2$CH$_2$CO—, wherein $R^6$ is an optionally esterified or amidated carboxyl group.

Alkyl is a straight or branched radical comprised of 1 to 7 carbon atoms unless otherwise specified, exemplified by methyl, ethyl, propyl, butyl, pentyl, hexyl or heptyl or an isomer. Lower alkyl is a radical of 1 to 4 carbon atoms.

An optionally esterified or amidated carboxyl group is the carboxyl group itself or a carboxyl group esterified with a lower alkanol, such as methanol, ethanol, propanol, butanol, or the carbamoyl group, which, on the nitrogen atom, is unsubstituted or monosubstituted or di-substituted by alkyl, especially lower alkyl, aryl, particularly phenyl, or arylalkyl, particularly benzyl. The carbamoyl group may also be substituted with an alkylidene radical such as butylidene or pentylidene radical. In addition, the carbamoyl group $R^5$ may also be substituted with a carbamoylmethyl group on the nitrogen atom.

Particularly preferred compounds are those of Formula II wherein R and $R^1$ are the same or different and are hydrogen or an acyl radical containing from 1 to 22 carbon atoms; $R^2$ is methyl; $R^3$ is hydrogen; X is L-alanyl, Y is D-isoglutaminyl, and n is 0.

A different preferred group of glycopeptides are the compounds of Formula II wherein R and $R^1$ are hydrogen or acyl of 1 to 22 carbon atoms, $R^2$ is methyl, $R^2$ is hydrogen, $R^4$ is methyl or butyl, and X is L-valyl, L-seryl, L-alanyl, L-threonyl or L-α-aminobutyryl.

Specific examples include the following compounds:

N-acetylmuramyl-L-α-aminobutyryl-D-isoglutamine;
6-0-stearoyl-N-acetylmuramyl-L-α-aminobutyryl-D-isoglutamine;
N-acetylmuramyl-L-threonyl-D-isoglutamine;
N-acetylmuramyl-L-valyl-D-isoglutamine;
N-acetylmuramyl-L-alanyl-D-glutamine n-butyl ester;
N-acetyl-desmethyl-D-muramyl-L-alanyl-D-isoglutamine;
N-acetylmuramyl-L-alanyl-D-glutamine;
N-acetylmuramyl-L-seryl-D-isoglutamine;
N-acetyl(butylmuramyl)-L-α-aminobutyl-D-isoglutamine; and
N-acetyl(butylmuramyl)-L-alanyl-D-isoglutamine.

An effective amount of immunostimulating glycopeptide is that amount which effects an increase in antibody titer level when administered in conjunction with an antigen over that titer level observed when the glycopeptide has not been co-administered (typically in the range of 0.0001 to 10% of the total composition). As can be appreciated, each glycopeptide may have an effective dose range that may differ from the other glycopeptides. Therefore, a single dose range cannot be prescribed which will have a precise fit for each possible glycopeptide within the scope of this invention. However, as a general rule, the glycopeptide will preferably be present in the vaccine in an amount of between 0.001 and 5% (w/v). A more preferred amount is 0.01 to 3% (w/v).

Most of the immunostimulating glycopeptides discussed above are essentially hydrophilic compounds. Accordingly, they are intended for use with a separate emulsifying agent (which can be, as discussed above, also an immunostimulating agent). In some case, the above-described compounds have a lipophilic character, such as the compounds comprising fatty acid substituents and/or aryl substituents on the sugar moiety, particularly those containing one or more acyl radicals containing from 14 to 22 carbon atoms, particularly those containing more than 1 such acyl substituent. However, it is also possible to achieve lipophilic character in a muramyl peptide by providing a lipid moiety linked through the carboxylate group or side chains of the peptide moiety. In particular, lipid groups joined to the peptide moiety through the terminal carboxylate group represent a preferred grouping of compounds. This linkage can readily be provided either directly, such as by forming an ester linkage between the terminal carboxylate and a fatty alcohol containing from 14 to 22 carbon atoms, or by using a bifunctional linking group, such as ethanolamine, to link the carboxylate through either a ester or amide linkage to a lipid. Particularly preferred in this embodiment of the invention are phospholipids, as the phosphate groups provide a readily linkable functional group. Diacylphospho-glycerides provide one such readily linkable phospho-lipid. Phosphatidyl ethanolamine, a readily available, naturally occurring compound, can be easily linked to the terminal carboxylate of the peptide moiety through an amide bond. Other lipids to the terminal carboxyl include acylglycerols, phosphatidyl choline, phosphatidyl serine, phosphatidyl inositol, phosphatidylglycerol, cardiolipin, and sphingomyelin.

A number of preferred amphipathic immunostimulating peptides are those having Formula III below:

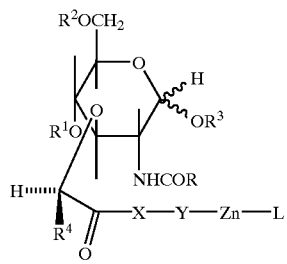

wherein R, $R^1$–$R^4$, X, Y, Z and n have the previously described meanings. L represents a lipid moiety, such as the lipid moieties described above.

In summary, the muramic acid moiety and the peptide moiety of the molecule together provide a hydrophilic moiety. A lipophilic moiety is also present in the molecule, lipophilicity generally being provided by a long-chain hydrocarbon group, typically present in the form of a fatty acid. The fatty acid or other hydrocarbon-containing radical can be attached to a hydroxyl group of the sugar or can be linked to the peptide portion of the molecule either directly, such as by reacting a fatty acid with a free amino group present in the peptide moiety, or through a linking group, such as a hydroxyalkylamine that forms a link between a carboxylic acid group of the peptide through amide bond formation and a functional group in a lipid, such as a phosphate group. Phospholipid moieties are particularly preferred for use in forming lipophilic muramyl peptides. A group of preferred compounds include muramyl dipeptides and tripeptides linked to a phospholipid moiety through a hydroxyalkylamine moiety. An example, and a particularly preferred compound, is N-acetylmuramyl-L-alanyl-D-isoglutaminyl-L-alanine-2-[1,2-dipalmitoyl-sn-glycero-3-(hydroxyphosphoryloxy)]ethylamide (abbreviated MTP-PE).

The adjuvant formulations are generally prepared from the ingredients described above prior to combining the adjuvant with the antigen that will be used in the vaccine. The word antigen refers to any substance, including a protein or protein-polysaccharide, protein-lipopolysaccharide, polysaccharide, lipopolysaccharide, viral subunit, whole virus or whole bacteria which, when foreign to the blood stream of an animal, on gaining access to the tissue of such an animal stimulates the formation of specific antibodies and reacts specifically in vivo or in vitro with a homologous antibody. Moreover, it stimulates the proliferation of T-lymphocytes with receptors for the antigen and can react with the lymphocytes to initiate the series of responses designated cell-mediated immunity.

A hapten is within the scope of this definition. A hapten is that portion of an antigenic molecule or antigenic complex that determines it immunological specificity. Commonly, a hapten is a peptide or polysaccharide in naturally occurring antigens. In artificial antigens it may be a low molecular weight substance such as an arsanilic acid derivative. A hapten will react specifically in vivo or in vitro with homologous antibodies or T-lymphocytes. Alternative descriptors are antigenic determinant, antigenic structural grouping and haptenic grouping.

The formulation of a vaccine of the invention will employ an effective amount of an antigen. That is, there will be included an amount of antigen which, in combination with the adjuvant, will cause the subject to produce a specific and sufficient immunological response so as to impart protection to the subject from the subsequent exposure to virus, bacterium, fungus, mycoplasma, or parasite immunized against.

Antigens may be produced by methods known in the art or may be purchased from commercial sources. For example, U.S. Pat. Nos. 4,434,157, 4,406,885, 4,264,587, 4,117,112, 4,034,081, and 3,996,907, incorporated herein by reference, describe methods for preparing antigens for feline leukemia virus vaccines. Other antigens may similarly be prepared. Antigens within the scope of this invention include whole inactivated virus particles, isolated virus proteins and protein subunits, whole cells and bacteria, cell membrane and cell wall proteins, and the like. Vaccines of the invention may be used to immunize birds and mammals against diseases and infection, including without limitation cholera, diphtheria, tetanus, pertussis, influenza, measles, meningitis, mumps, plague, poliomyelitis, rabies, Rocky Mountain spotted fever, rubella, smallpox, typhoid, typhus, feline leukemia virus, and yellow fever.

No single dose designation can be assigned which will provide specific guidance for each and every antigen which may be employed in this invention. The effective amount of antigen will be a function of its inherent activity and purity. It is contemplated that the adjuvant compositions of this invention may be used in conjunction with whole cell or virus vaccines as well as with purified antigens or protein subunit or peptide vaccines prepared by recombinant DNA techniques or synthesis.

Since the adjuvant compositions of the invention are stable, the antigen and emulsion can mixed by simple shaking. Other techniques, such as passing a mixture of the adjuvant and solution or suspension of the antigen rapidly through a small opening (such as a hypodermic needle) readily provides a useful vaccine composition.

The invention now being generally described, the same will be better understood by reference to the following detailed examples which are provided by way of illustration and are not intended to be limiting of the invention unless so specified.

EXAMPLE 1

General Techniques

The following general techniques were used throughout the examples that follow, except where noted:

Materials

MTP-PE was provided by CIBA-GEIGY (Basel, Switzerland). Squalene and Tween 80 were obtained from Sigma Chemical Co. (St. Louis, Mo.). CFA and IFA were obtained from Gibco (Grand Island, N.Y.). Aluminum hydroxide (Rehsorptar) was obtained from Reheis Chemical Co. (Berkeley Heights, N.J.).

Preparation of Emulsions

Method 1—Syringe and needle. A mixture consisting of 4% squalene, 0.008% Tween 80, 250 µg/ml MTP-PE and antigen in phosphate buffered saline (PBS) was passed through a 23 gauge needle 6 times. This emulsion consisted of oil droplet sizes in the range of 10 microns and is termed MTP-PE-LO.

Method 2—Kirkland Emulsifier. The above mixture was passed through a Kirkland emulsifier five times. This emulsion consists of oil droplets primarily of 1–2 microns and is termed MTP-PE-LO-KE. The Kirkland emulsifier (Kirkland Products, Walnut Creek, Calif.) is a small-scale version of the commercial knife-edged homogenizer (e.g., Gaulin Model 30 CD and Rainnie Minilab Type 8.30 H) generating about 1000 psi in the working chamber.

Method 3—Microfluidizer. Mixtures containing 0.3–18% squalene and 0.2–1.0 mg/ml MTP-PE with or without Tween 80 were passed through the Microfluidizer (Model No. 110Y, Microfluidics Newton, Mass.) at 5,000–30,000 PSI. Typically, 50 ml of emulsion was mixed for 5 minutes or 100 ml for 10 minutes in the microfluidizer. The resulting emulsions consisted of oil droplets of 100–750 nm depending on squalene, MTP-PE, and detergent concentration and microfluidizer operating pressure and temperature. This formulation is termed MTP-PE-LO-MF.

Antigen was added to the adjuvant formulations above after preparation. The antigen and emulsion were mixed by shaking. When using CFA and IFA, antigen in PBS was mixed with an equal volume of either CFA or IFA. The mixture was emulsified by passing through a hypodermic needle until a thick, emulsion was achieved.

Antigens

Herpes simplex virus (HSV) rgD2 is a recombinant protein produced genetically engineered Chinese hamster ovary cells. This protein has the normal anchor region truncated, resulting in a glycosylated protein secreted into tissue culture medium. The gD2 was purified in the CHO medium to greater than 90% purity. Human immunodeficiency virus (HIV) env-2–3 is a recombinant form of the HIV enveloped protein produced in genetically engineered *Saccharomyces cerevisae*. This protein represents the entire protein region of HIV gp120 but is non-glycosylated and denatured as purified from the yeast. HIV gp120 is a fully glycosylated, secreted form of gp120 produced in CHO cells in a fashion similar to the gD2 above.

Immunization of Animals

Mice were injected with the various adjuvant/antigen formulations by intraperitoneal, intramuscular, or subcutaneous routes. Guinea pigs were immunized by footpad or intramuscular routes. Rabbits, goats, and baboons were immunized by the intramuscular routes.

Analysis of Immune Response

Antibody titers against the immunizing antigen were determined by enzyme linked immunosorbent assay (ELISA).

EXAMPLE 2

MTP-PE-LO Formulation in Large Animals

Comparative Example

A number of experiments were carried out, first with the HIV env 2–3 antigen and later with the HSV gD protein, using the MTP-PE-LO formulation to stimulate immunity in large animals. These experiments are outlined below.

1. HIV env 2–3 a. Guinea pigs. Guinea pigs were immunized monthly with 50 µg/dose of env 2–3 by either the footpad or intramuscular route. The vaccine was administered with either the MTP-PE-LO formulation (4% Squalene, 0/008% Tween 80, 50 pg/dose MTP-PE) or absorbed to alum (0.7% aluminum hydroxide). Sera were collected one week after each immunization and analyzed for anti-env 2–3 antibody by ELISA. The results are shown in Table 1. The MTP-PE-LO formulation gave high anti-env 2–3 titers when delivered both intramuscularly and in the footpad. In contrast, alum gave much lower antibody titers by both routes. This experiment illustrates the effectiveness of the MTP-PE-LO formulation in guinea pigs.

TABLE 1

Comparison of Different Adjuvants, As a Function of Injection Route,
In Eliciting Env 203 Specific Antibodies[a]

| Adjuvant Group | Animal # | Route | Env 2-3 ELISA Titers Immunization Number | | | | | | |
|---|---|---|---|---|---|---|---|---|---|
| | | | Zero | Two | Three | Four | Five | Six | Seven |
| MTP-PE | 839 | FP | <<100[c] | 135,500 | 382,100 | 343,100 | 401,800 | 338,000 | 382,700 |
| 4% Squalene | 840 | FP | <<100 | 331,700 | 588,700 | 542,300 | 392,900 | 359,000 | 292,100 |
| 0.008% | 841 | FP | <<100 | 247,800 | 330,900 | 301,100 | 285,800 | 334,400 | 383,700 |
| Tween | 842 | FP | <<100 | 108,100 | 570,300 | 694,300 | 344,400 | 289,800 | 220,300 |
| | 843 | FP | <<100 | 65,00 | — | — | — | — | — |
| | 844 | FP | <<100 | 25,000 | — | — | — | — | — |
| | (average) | (FP) | (<<100) | (152,000) | (468,000) | (470,000) | (356,000) | (330,000) | (295,000) |
| MTP-PE | 845 | IM | <<100 | 12,300 | 19,600 | 23,800 | 15,100 | 20,000 | 27,300 |
| 4% Squalene | 846 | IM | <<100 | 10,400 | 20,500 | 43,600 | 44,800 | 121,100 | 42,000 |
| 0.008% | 847 | IM | <<100 | 29,700 | 80,000 | 136,800 | 156,000 | 144,500 | 164,400 |
| Tween | 848 | IM | <<100 | 447,000 | 640,000 | 400,000 | 71,000 | 674,000 | 533,000 |
| | 849 | IM | 350 | 10,600 | 78,700 | 311,000 | 533,000 | nt | 200,000 |
| | 850 | IM | <<100 | 340,000 | — | — | — | — | — |
| | (average) | (IM) | (<<100) | (142,000) | (168,000) | (183,000) | (164,000) | (240,000) | (193,000) |
| Alum | 863 | FP | <<100 | <<100 | nt | nt | nt | nt | nt |
| | 864 | FP | <<100 | 2,500 | 4,100 | 86,000 | 47,700 | 21,000 | 16,000 |
| | 865 | FP | <<100 | 2,400 | 26,400 | 80,400 | 83,500 | 39,200 | 4,500 |
| | 866 | FP | <<100 | 15,100 | 103,900 | 124,100 | 107,100 | 56,700 | 16,800 |
| | 867 | FP | <<100 | 2,200 | 8,800 | 14,500 | 11,900 | 11,400 | 12,300 |
| | 868 | FP | <<100 | 6,500 | 44,500 | 34,000 | 18,800 | 12,800 | |
| | (average) | (FP) | <<100 | (5,700) | (38,000) | (68,000) | (54,000) | (28,000) | (12,000) |
| Alum | 869 | IM | <<100 | <<100 | 300 | 2,600 | 2,000 | 1,600 | 2,300 |
| | 870 | IM | <<100 | <<100 | 130 | 220 | 330 | 270 | 300 |
| | 871 | IM | <<100 | <<100 | 1,200 | 4,300 | 4,900 | 3,000 | 1,600 |
| | 872 | IM | <<100 | <<100 | 300 | 900 | 920 | 770 | 1,700 |
| | 873 | IM | <<100 | <<100 | 990 | 41,100 | 79,800 | 27,900 | 15,500 |
| | 874 | IM | <<100 | <<100 | 940 | 17,300 | 13,200 | 10,600 | 8,600 |
| | (average) | (IM) | (<<100) | (<<100) | (640) | (11,000) | (17,000) | (7,000) | (5,000) |

[a]Guinea pigs were immunized monthly with 50 "'m'"g/dose of env 2-3 with the different adjuvants by either the footpad (FP) or intramuscular (IM) route. Sera were collected one week following each immunization.
b. —; no data obtained due to death of the animal.
[c]<<100; no detectable ELISA signal at 1:100 serum dilution.
d. nt = not tested b. Goats. Pairs of goats received 1 mg of env 2–3 on primary immunizations and 500 μg on secondary immunization with the MTP-PE-LO formulation containing various amounts of MTP-PE from 0 to 500 μg. Positive control animals received the primary immunization with CFA and the secondary immunization with IFA. One group also received 100 μg env 2–3 in the primary immunization followed by 50 μg in the secondary immunization with the MTP-PE-LO formulation containing 100 μg MTP-PE. As shown in Table 2, both goats receiving Freund's adjuvant showed high antibody titers ranging from 2700 to 62,800. In contrast, most of the goats receiving the MTP-PE-LO formulation were negative for anti-env 2–3 antibody. Animals that did respond only developed titers in the 100–600 range. These results are in stark contrast to the guinea pig data above.

TABLE 2

Antibody Responses of Goats Immunized
With Env 2-3 and Various Doses of MTP-PE

| Adjuvant Formulation | Animal Number | Env 2-3 ELISA Titer Immunization | | |
|---|---|---|---|---|
| | | None | One | Two |
| Freund's | 2295 | [b]<<100 | 43,200 | 62,800 |
| | 2296 | <<100 | 2,700 | 7,500 |
| [a]ST + 0 μg | 2297 | <<100 | [c]<100 | <100 |
| MTP-PE | 2298 | <<100 | 100 | 300 |
| ST + 20 μg | 2290 | <<100 | <100 | <100 |
| MTP-PE | 2302 | <<100 | 100 | 200 |
| ST + 50 μg | 2301 | <<100 | <<100 | <100 |
| MTE-PE | 2302 | <<100 | <<100 | <100 |
| ST + 100 μg | 2303 | <<100 | <<100 | 100 |
| MTP-PE | 2304 | <<100 | <<100 | <100 |
| ST + 250 μg | 2305 | <<100 | <<100 | 600 |
| MTP-PE | 2306 | <<100 | <<100 | <100 |
| ST + 500 μg | 2307 | <<100 | <100 | <100 |
| MTP-PE | 2308 | <<100 | <<100 | <<100 |
| ST + 100 μg | 2309 | 200 | 500 | 200 |
| MTP-PE | 2310 | <<100 | <100 | <<100 |

[a]ST is the low oil formulation; 4% Squalene, 0.008% Tween 80.
[b]<<100 indicates an env 2-3 ELISA titer that was not above background at a 1/100 serum dilution.
[c]<100 indicates an env 2-3 ELISA value at a 1/100 serum dilution that was above background but less than the half maximal signal in the assay.

c. Dogs. Beagle dogs were immunized with either 250 μg of env 2–3 in MTP-PE-LO (100 μg MTP-PE) or with the MTP-PE-LO formulation alone at three week intervals. Ten days after each immunization the animals were bled and anti-env 2–3 antibody titers were determined by ELISA. Table 3 shows that the two dogs receiving env 2–3 plus adjuvant did develop anti-env 23 titers, but these titers failed to reach the levels seen in guinea pigs (maximum titers 1700 and 6300 for the two immunized animals). In addition, these animals failed to develop virus neutralizing antibodies to either the homologous (SF2) or heterologous (BRU or Zr6) HIV strains.

TABLE 3

ELISA and Neutralizing Antibody Titers of Sera From Beagle Dogs Immunized With Env 2-3 In MTP-PE-LO Adjuvant[a]

| Animal # | Immunized with | Immunization # | ELISA titer | Env 2-3 Neutralization titers | | |
|---|---|---|---|---|---|---|
| | | | | HIV-SF2 | HIV-BRU | HIV-Zr6 |
| 1375 | env 2-3 | pre-bleed | [b]<<100 | [c]<20 | <20 | <20 |
| | MTP-PE-LO 100 μg MTP-PE | 2 | 1,300 | <20 | <20 | <20 |
| | | 3 | 1,700 | <20 | <20 | <20 |
| | | 4 | 900 | <20 | <20 | <20 |
| | | 5 | 400 | <20 | <20 | <20 |
| | | 6 | 300 | <20 | <20 | <20 |
| | | 7 | 300 | <20 | <20 | <20 |
| 1376 | env 2-3 | pre-bleed | <<100 | <20 | <20 | <20 |
| | MTP-PE-LO 100 μg MTP-PE | 2 | 3,500 | <20 | <20 | <20 |
| | | 3 | 6,300 | <20 | <20 | <20 |
| | | 4 | 5,100 | <20 | <20 | <20 |
| | | 5 | 2,100 | <20 | <20 | <20 |
| | | 6 | 2,200 | <20 | <20 | <20 |
| | | 7 | 2,000 | <20 | <20 | <20 |
| 1377 | MTP-PE-LO O-MTP-PE control | pre-bleed | <<100 | <20 | <20 | <20 |
| | | 2 | <<100 | <20 | <20 | <20 |
| | | 3 | <<100 | <20 | <20 | <20 |
| | | 5 | <<100 | <20 | <20 | <20 |
| | | 6 | <<100 | <20 | <20 | <20 |
| | | 7 | <<100 | <20 | <20 | <20 |
| 1378 | MTP-PE-LO O-MTP-PE control | pre-bleed | <<100 | <20 | <20 | <20 |
| | | 2 | <<100 | <20 | <20 | <20 |
| | | 3 | <<100 | <20 | <20 | <20 |
| | | 4 | <<100 | <20 | <20 | <20 |
| | | 5 | <<100 | <20 | <20 | <20 |
| | | 6 | <<100 | <20 | <20 | <20 |
| | | 7 | <<100 | <20 | <20 | <20 |

[a]Dogs received 250 μg of env 2-3 in Biocine adjuvant (100 μg MTP-PE) intramuscularly every 21 days. Blood samples were collected 10 days following each injection.
[b]ELISA titers of <<100 are listed when no signal was detected at a 1/100 serum dilution.
[c]Neutralization titers of <20 indicate that no neutralization was observed at the most concentrated serum dilution tested (1/20).

d. Pigs. Pigs were immunized with 1 mg env 2–3 with MTP-PE-LO (100 μg MTP-PE) every 21 days. Control animals received the adjuvant alone. Ten days after each immunization the animals were bled, and anti-env 2–3 antibody titers were determined by ELISA. The results in Table 4 show that the two immunized animals developed only low anti-env 2 titers (140 and 100, respectively) and no detectable virus neutralizing titers against either the homologous strain (SF2) or heterologous strains (BRU or Zr6).

TABLE 4

ELISA and neutralizing antibody titers of swine immunized with env 2-3 MTP-PE-LO adjuvant.[a]

| Animal Number | Antigen | Immunization Number | env 2-3 ELISA titer | Neutralizing titer on: | | |
|---|---|---|---|---|---|---|
| | | | | HIV-SF2 | HIV-BRU | HIV-Zr6 |
| 1371 | Env 2-3 | pre-bleed | [b]<<50 | [d]<20 | <20 | <20 |
| | | 2 | [c]<50 | <20 | <20 | <20 |
| | | 3 | 70 | <20 | <20 | <20 |
| | | 4 | 70 | <20 | <20 | <20 |
| | | 5 | 80 | <20 | <20 | <20 |
| | | 6 | 70 | <20 | <20 | <20 |
| | | 7 | 140 | <20 | <20 | <20 |
| 1372 | Env 2-3 | pre-bleed | <<50 | <20 | <20 | <20 |
| | | 2 | 100 | <20 | <20 | <20 |
| | | 3 | 70 | <20 | <20 | <20 |
| | | 4 | 70 | <20 | <20 | <20 |
| | | 5 | 60 | <20 | <20 | <20 |
| | | 6 | 90 | <20 | <20 | <20 |
| | | 7 | 90 | <20 | <20 | <20 |
| 1373 | Adjuvant Control | pre-bleed | <<50 | <20 | <20 | <20 |
| | | 2 | <<50 | <20 | <20 | <20 |
| | | 3 | <<50 | <20 | <20 | <20 |
| | | 4 | <<50 | <20 | <20 | <20 |
| | | 5 | <<50 | <20 | <20 | <20 |
| | | 6 | <<50 | <20 | <20 | <20 |
| | | 7 | <<50 | <20 | <20 | <20 |
| 1374 | Adjuvant Control | pre-bleed | <<50 | <20 | <20 | <20 |
| | | 2 | <<50 | <20 | <20 | <20 |
| | | 3 | <<50 | <20 | <20 | <20 |
| | | 4 | <<50 | <20 | <20 | <20 |
| | | 5 | <<50 | <20 | <20 | <20 |
| | | 6 | <<50 | <20 | <20 | <20 |
| | | 7 | <<50 | <20 | <20 | <20 |

[a]Swine received 1 mg of env 2-3 in Biocine adjuvant (100 μg MTP-PE) intramuscularly every 21 days. Sera were collected 10 days following each immunization.
[b]Showing no signal at 1/50 serum dilution are listed as having titers of <<50.
[c]Low but detectable signal at 1/50 serum dilution.
[d]No neutralization seen at a 1/20 serum dilution, the most concentrated dilution tested.

e. Monkeys. Rhesus macaques were immunized every 30 days with 250 μg of env 2–3 with MTP-PE-LO (100 μg MTP-PE). Control animals received the adjuvant formulation alone. One week after each immunization, the animals were bled and anti-env 2–3 antibody titers were determined by ELISA. Table 5 shows that, similar to the dogs, all animals developed antibody titers to env 2–3, but these titers only ranged from 300–3100, far lower than seen previously with guinea pigs.

TABLE 5

Titers of env 2-3 specific antibodies in sera from Rhesus macaques immunized with env 2-3 in MTP-PE-LO adjuvant.[a]

| Animal Antigen | Number | Prebleed | Immunization 1 | 2 | 3 | 4 | 5 | 6 |
|---|---|---|---|---|---|---|---|---|
| Env 2-3 | 1189 | <<100 | <<100 | 300 | 700 | 400 | 400 | 300 |
| | 1190 | <<100 | <<100 | <<100 | 800 | 800 | 900 | 500 | |
| | 1191 | <<100 | <<100 | 1,200 | 2,000 | 1,300 | 1,900 | 3,100 | |
| | 1192 | <<100 | <<100 | 500 | 900 | 400 | 400 | 500 | |
| (average) | | <<100 | <<100 | 780 | 1,100 | 700 | 900 | 1,100 | |
| Adjuvant Control | 1197 | <<100 | <<100 | <<100 | <<100 | <<100 | <<100 | <<100 |
| | 1198 | <<100 | <<100 | <<100 | <<100 | <<100 | <<100 | <<100 | |
| | 1199 | <<100 | <<100 | <<100 | <<100 | <<100 | <<100 | <<100 | |
| | 1978 | <<100 | <<100 | <<100 | <<100 | <<100 | <<100 | <<100 | |
| (average) | | <<100 | <<100 | <<100 | <<100 | <<100 | <<100 | <<100 | |

Animals received 250 mg of antigen in Biocine adjuvant (100 mg MTP-PE) intramuscularly every 30 days. Sera were collected one week following each immunization.

2. HSv gD a. Goats. A series of adjuvant formulations were tested with gD2 in goats. Animals were immunized with 100 μg of gD2 with the various adjuvants every 21 days. Ten days after the second and third immunizations the animals were bled and anti-gD2 titers were determined by ELISA. The following adjuvant formulations were used. CFA (1°) followed by IFA (2° & 3°), IFA containing 100 μg MTP-PE), 0.8 mg/ml aluminum hydroxide (alum), MTP-PE-LO (100 μg MTP-PE), MTP-PE-LO-KE (100 μg MTP-PE), and MTP-PE-LO-KE (12% squalene, 5.0 mg MTP-PE). The ELISA results are shown in Table 6. One CFA/IFA animal, both MTP-PE/IFA animals, and one MTP-PE-LO-KE (5 mg MTP-PE) animal developed high antibody titers (2187–13, 172). One CFA/IFA animal, both alum animals, and one MTP-PE-LO-KE (5 mg MTP-PE) animals developed moderate antibody titers (5691489). The MTP-PE-LO animals and the MTP-PE-LO-KE animals developed low anti-gD2 titers (46–323). Thus, as with env 2 noted above, the MTP-PE-LO formulation fails to elicit high antibody titers in goats. Modifying the emulsion by using the Kirkland emulsifier (1–2 mm oil droplet sizes) did not improve the adjuvant performance. Vast increases in MTP-PE (to 5.0 mg) dose appeared to improve the adjuvant performance.

TABLE 6

Adjuvant effectiveness with gD2 in the goats.

| Group | Animal | Adjuvant | ELISA Titer After 2 Immunizations | 3 Immunizations |
|---|---|---|---|---|
| 1 | 3606 | CFA/IFA | 2187 | 13172 |
| | 3609 | | 738 | 770 |
| 2 | 3610 | Alum | 1489 | 781 |
| | 3611 | | 921 | 522 |
| 3 | 3612 | MTP-PE-LO (100 μg MTP-PE) | 77 | 194 |
| | 3613 | | 145 | 323 |
| 4 | 3614 | MTP-PE-LO-KE (100 μg MTP-PE) | 123 | 227 |

TABLE 6-continued

Adjuvant effectiveness with gD2 in the goats.

| Group | Animal | Adjuvant | ELISA Titer After 2 Immunizations | 3 Immunizations |
|---|---|---|---|---|
| | 3615 | | 56 | 46 |
| 5 | 3624 | MTP-PE-LO-KE (12% squalene, 5.0 mg MTP-PE) | 142 | 569 |
| | | | 615 | 2291 | b. Baboons. Juvenile baboons were immunized with gD2 formulated with alum, MTP-PE-LO-KE, MTP/IFA and IFA alone. In addition a dose ranging study for gD2 combined with alum and MTP-PE-LO-KE was done. Baboons of 2–3 yr (3.4 to 12 kg) were immunized intramuscularly in the thigh three times at three-week intervals. Sera were collected 3 weeks after the first two immunizations and 2 weeks after the final vaccine dose for determination of gD-specific antibody by ELISA. Whole blood was drawn at each of these time points for complete blood cell analyses (CBC). Baboons immunized with 100 μg of gD2 bound to alum developed anti-gD2 mean antibody titers of 3349±550. There was no significant difference in titers for the three antigen doses tested, 10, 25, 100 μg of protein. Antibody responses in 4 groups of animals who received 10 or 100 μg of gD2 emulsified with 250 μg of MTP-PELO-KE or 25 ug of gD2 emulsified with 50 μg or 1000 μg of MTP-PE-LO-KE were similar to those of the groups immunized with gD2/alum (means ranging from 1300 to 3900) vaccinated with 25 μg of gD2 and 250 μg of MTP-PE-LO-KE. MTP-PE emulsified with IFA was used as a positive control group in this experiment. Animals immunized with alum had titers which were about 1% those of the MTP/IFA vaccines and MTP-PE-LO-KE immunized animals had titers ranging from 0.5 to 1.3 those of MTP/IFA. These results are summarized in Table 7.

TABLE 7

HSV vaccine trial in baboons: antibody titers[a]

| Group | Adjuvant Composition | gD2 Dose (mg) | Dose (mg) | ELISA Titers[b] | | | % of MTP-PE/IFA[c] |
|---|---|---|---|---|---|---|---|
| | | | | 1° Bleed | 2° Bleed | 3° Bleed | |
| 1 | Alum | 400 | 10 | 287 (+123) | 1002 (+366) | 1566 (+350) | 0.6 |
| 2 | Alum | 400 | 25 | 1075 (+785) | 880 (+343) | 1993 (+1156) | 0.8 |
| 3 | Alum | 400 | 100 | 720 (+184) | 1882 (+489) | 3349 (+550) | 1.3 |
| 4 | MTP-PE/LO | 50 | 25 | 140 (+63) | 788 (+331) | 1320 (+430) | 0.5 |
| 5 | MTP-PE/LO | 250 | 10 | 217 (+103) | 2490 (+995) | 3244 (+1582) | 1.3 |
| 6 | MTP-PE/LO | 250 | 100 | 57 (+34) | 925 (+254) | 2439 (+510) | 1.0 |
| 7 | MTP-PE/LO | 1000 | 25 | 91 (+70) | 1097 (+565) | 3883 (+2401) | 1.6 |
| 8 | MTP-PE/IFA | 250 | 25 | 24,101 (+5423) | 62,775 (+28,634) | 250,382 (+64,771) | 100 |
| 9 | IFA | | 25 | 2591 (+2280) | 7631 (+6563) | 66,132 (+75,095) | 26.4 |

[a]All animals immunized with gD2 by IM delivery in the thigh; 4 animals/group
[b]50% endpoint antibody titer, geometric mean + SE
[c]Fraction of animals with a positive gD2-specific lymphoproliferative response defined as a stimulation index >3.0.

No adverse reactions to the vaccines were noted in any of the animals, and the CBC profiles were normal.

These small droplet size emulsions were then tested as adjuvants for vaccine antigens in goats and baboons.

TABLE 8

Composition and Physical Parameters of MTP-PE-Squalene Emulsions made with the Microfluidizer

| Formulation | MTP-PE (mg/ml) | Squalene % | Tween 80 % | Mannitol % | Aqueous Phase | Temp (° C.) | Pressure (KPSI) | Size (m) |
|---|---|---|---|---|---|---|---|---|
| A | .01 | 2 | .004 | 0 | $H_2O$ | 40° | 5 | .23 |
| B | 0.2 | 2 | .004 | 0 | $H_2O$ | 40 | 5 | .17 |
| C | 1.0 | 2 | 0.16 | 5 | $H_2O$ | 0 | 10 | .19 |
| D | 0.5 | 2 | 0 | 5 | $H_2O$ | 40 | 10 | .16 |
| E | 0.5 | 2 | 0 | 0 | $H_2O$ | 40 | 10 | .17 |
| F | 1.0 | 4 | 0 | 0 | $H_2O$ | 30 | 10 | .19 |
| G | 1.0 | 4 | 0 | 0 | $H_2O$ | 20 | 10 | .20 |
| H | 1.0 | 4 | 0 | 0 | $H_2O$ | 0 | 15 | .20 |
| I | 1.0 | 4 | 0 | 0 | $H_2O$ | 0 | 10 | .29 |
| J | 1.0 | 4 | 0 | 0 | $H_2O$ | 0 | 5 | .39 |
| K | 1.0 | 4 | .16 | 0 | $H_2O$ | 0 | 10 | .22 |
| L | 1.0 | 4 | .016 | 0 | $H_2O$ | 0 | 10 | .27 |
| M | 1.0 | 6 | 0 | 0 | $H_2O$ | 0 | 10 | .29 |

EXAMPLE 3

MTP-PE-LO Formulation Effective in Stimulating Immunity in Large Animals

As demonstrated in Example 2, MTP-PE-LO formulations that were prepared with a syringe and needle (~10 micron droplet size) and the Kirkland emulsifier (1–2 micron droplet size) failed to give good immunostimulation to vaccine antigens in large animals and humans (human data not shown). The microfluidizer model 110Y was used to generate small-droplet-size, stable emulsions. This machine is a high pressure (5000–30,000 PSI) submerged jet type emulsifier. A series of emulsions were prepared varying in size and stability based on the concentrations of squalene, Tween 80, and MTP-PE and the physical parameters of temperature and operating pressure. Examples of different emulsions made with the microfluidizer are given in Table 8. By changing the physical parameters and emulsion composition, oil droplet sizes from 1 micron to less than 0.2 microns can be achieved. As demonstrated in Table 8, parameters that decrease emulsion droplet size are increased detergent, increased MTP-PE to squalene ratio, increased operating pressure, and increased operating temperature.

1. HSV gD2 in Goats

The first microfluidizer used with the gD2 antigen was a 4% squalene, 100 μg/ml MTP-PE emulsion without Tween 80 (MTP-PE-LO-MF #13; number designations of MTP-PE-LO-MF formulations are arbitrary and are intended only for use as reference numbers). This material was made at low pressure in the microfluidizer and had an oil droplet size of about 0.8 microns. Goats were immunized intramuscularly with 100 μg of gD2 in this formulation three times at 21 day intervals. Goats immunized with 100 μg gD2, in CFA for primary and IFA for secondary and tertiary immunizations served as controls. Ten days after the second and third immunization the animals were bled and anti-gD2 antibody titers were determined by ELISA. The results are shown in Table 9. Both animals receiving the MTP-PE-LO-MF showed significant anti-gD2 titers. These titers 1661–2966 were intermediate compared to the titers of the two CFA/IFA control goats (140–24,269). The MTP-PE-LO-MF animals showed titers that were significantly higher than goats that had received MTP-PE-LO formulations prepared in a syringe and needle or in the Kirkland emulsifier (see Table 6). In a second experiment in goats, 100 μg gD2 was administered every 21 days with MTP-PE-LO-MF #16. This formulation consisted of 4% squalene, 500 μg/ml MTP-PE and O Tween 80. The oil droplet size of this emulsion was 0.5–0.6 microns. As seen in Table 10, this formulation appeared to give even higher antibody titers than the previous formulation. Thus, reducing the oil droplet size and/or increasing the MTP-PE improves the adjuvant performance of this emulsion.

TABLE 9

Test of MTP-PE-LO-MF #13 as an adjuvant for gD2 in Goats

| Group | Animal Number | Adjuvant | Antigen | ELISA titer after: 2 Immunizations | 3 Immunizations |
|---|---|---|---|---|---|
| 1 | 4519 | CFA/IFA | gD2 (100 μg) | 9868 | 24269 |
|   | 4520 | " | gD2 (100 μg) | 140 | 980 |
| 2 | 4598 | MTP PE-LO-MF[a] | gD2 (100 μg) | 2966 | 2207 |
|   | 4599 | " | gD2 (100 μg) | 1661 | N.T.[b] |

[a]4% squalene, 100 μg/ml MTP-PE, O Tween 80, H₂O, about 0.8 micron oil droplet size.
[b]N.T. - Not tested. Animal died of causes unrelated to immunization.

TABLE 10

Test of MTP-PE-LO-MF #13 as an adjuvant for gD2 in Goats

| Animal Number | Adjuvant | Antigen | ELISA titer after: 2 Immunizations | 3 Immunizations |
|---|---|---|---|---|
| 5013 | MTP-PE-LO-MF #16 | gD2 (100 μg) | 1299 | 386 |
| 5014 | MTP-PE-LO-MF #16 | gD2 (100 μg) | 6657 | 2806 |
| 5015 | MTP-PE-LO-MF #16 | gD2 (100 μg) | 8206 | 1943 |
| 5016 | MTP-PE-LO-MF #16 | gD2 (100 μg) | 7886 | 1514 |

[a]MTP-PE-LO-MF #16 - 4% squalene, 500 μg/ml MTP-PE, O Tween 80, H₂O. Oil droplet size of 0.5–0.6 microns.

2. HIV env 2–3 and gp120 in Goats

Microfluidizer preparations were compared to CFA/IFA and the MTP-PE-LO-KE as adjuvants using the HIV antigen env 2–3 and gp120. Animals were immunized three times at 21-day intervals with 100 μg of the gp120 antigen in CFA(1°)/IFA(2° & 3°), MTP-PE-LO-MF #14 (4% squalene, 500 μg/ml MTP-PE, O Tween, phosphate buffered saline) MTP-PE-LO-KE (4% squalene, 100 μg MTP-PE, 0.008% Tween 80, phosphate buffered saline emulsified in the Kirkland emulsifier) and MTP-PE-LO-MF #15 (4% squalene, 100 μg MTP-PE, 0.008% Tween 80, phosphate buffered saline). Animals were also immunized with 100 pg of the HIV antigen env 2–3 in CFA/IFA and in MTP-PE-LO-MF #14. The animals were bled 10 days after the second and third immunization and anti-env 2–3 antibody titers were determined by ELISA. The results are shown in Table 11. With env 2–3, the animals immunized with the MTP-PE-LO-MF #14 formulation showed equivalent titer to CFA/IFA animals after two immunizations and higher titers than the CFA/IFA animals after three immunizations. With gp120 the results were not quite as clear. The MTP-PE-LO-MF #14 animals show much more variation than the CFA/IFA animals. Thus the mean titers for the microfluidizer group is lower than the CFA group, but individual animals receiving MTP-PE-LO-MF #14 did show titers as high as any animals in the CFA/IFA group. A direct comparison with gp120 of identical adjuvant components (4% squalene, 100 μg/ml MTP-PE, 0.008% Tween 80, phosphate buffered saline) emulsified by two different methods (Kirkland emulsifier vs. microfluidizer) illustrates the importance of the small droplet size in the emulsion. The Kirkland emulsifier group showed mean titer of 632 after these immunizations while the microfluidizer group showed mean titer of 3277.

TABLE 11

Test of MTP-PE-LO-MF as an adjuvant with HIV antigens env 2 and gp120

| Group | Animal Number | Adjuvant | Antigen | ELISA Titer after: 2 immunization | Genometric Mean + SE | 3 immunization | Genometric Mean + SE |
|---|---|---|---|---|---|---|---|
| 1 | 5018 | CFA/IFA | gp120 (100 mg) | 900 | 1861 + 539 | 7300 | 6630 + 996 |
|   | 5019 | " | gp120 (100 mg) | 3700 |  | 5700 |  |
|   | 5020 | " | gp120 (100 mg) | 2000 |  | 7100 |  |
|   | 5021 | " | gp120 (100 mg) | 1800 |  | 3400 |  |
| 2 | 5022 | CFA/IFA | env 2 (100 mg) | 2400 | 2235 + 680 | 3000 | 5074 + 1378 |
|   | 5023 | " | env 2 (100 mg) | 4600 |  | 3400 |  |
|   | 5024 | " | env 2 (100 mg) | 2400 |  | 8900 |  |
| 3 | 5026 | MTP-PE-LO-MF #14[a] | gp120 (100 mg) | 0 | 101 + 1089 | 800 | 1324 + 994 |
|   | 5027 | " | gp120 (100 mg) | 300 |  | 500 |  |
|   | 5029 | " | gp120 (100 mg) | 3407 |  | 5800 |  |
| 4 | 5030 | MTP-PE-LO-MF #14[a] | env 2 (100 mg) | 7900 | 2351 + 1688 | 19,500 | 9896 + 2493 |
|   | 5031 | " | env 2 (100 mg) | 4600 |  | 6600 |  |
|   | 5032 | " | env 2 (100 mg) | 300 |  | 6900 |  |
|   | 5033 | " | env 2 (100 mg) | 2800 |  | 10,800 |  |
| 5 | 5034 | MTP-PE-LO-KE[b] | gp120 (100 mg) | 0 | 721 + 416 | 600 | 632 + 32 |
|   | 5035 | " | gp120 (100 mg) | 1400 |  | 600 |  |
|   | 5037 | " | gp120 (100 mg) | 400 |  | 700 |  |

TABLE 11-continued

Test of MTP-PE-LO-MF as an adjuvant with HIV antigens env 2 and gp120

| | | | | ELISA Titer after: | | | |
|---|---|---|---|---|---|---|---|
| Group | Animal Number | Adjuvant | Antigen | 2 immunization | Genometric Mean + SE | 3 immunization | Genometric Mean + SE |
| 6 | 5038 | MTP-PE-LO-MF #15[c] | gp120 (100 mg) | 1000 | 10 + 333 | 5100 | 3277 + 767 |
| | 5040 | " | gp120 (100 mg) | 0 | | 2300 | |
| | 5041 | " | gp120 (100 mg) | 0 | | 3000 | |

[a]MTP-PE-LO-MF #14 - 4% squalene, 500 mg/ml MTP, 0 Tween, phosphate buffered saline.
[b]MTP-PE-LO-KE - 4% squalene, 100 mg/ml MTP-PE, 0.008% Tween 80 phosphate buffered saline emulsified in the Kirkland emulsifier.
[c]MTP-PE-LO-MF #15 - 4% squalene, 100 mg/ml MTP-PE, 0.008% Tween 80, phosphate buffered saline.

3. HIV env 2–3 and gp120 in Baboons

MTP-PE-LO-MF #1 (2% squalene, 500 µg/ml MTP-PE, O Tween 80, H20, oil droplet size ~0.17 microns) was tested as an adjuvant with the HIV antigens env 2–3 and gp120 in baboons. MTP-PE in IFA and alum were used as controls. Animals were immunized at one month intervals. Two weeks after the second immunization, the animals were bled and anti-env 2–3 antibody virus neutralizing titers were determined. The results are shown in Table 12. Antibody titers against gp120 were higher with MTP-PE-LO-MF #1 than with MTP-PE-IFA. Anti-env 2–3 titers were similar in the MTP-PE-IFA and MTP-PE-LO-MF #1 groups. Anti-gp120 titers achieved with alum were in the same range as with MTP-PE-LO-MF #1 but anti env 2–3 titers achieved with alum appear lower than with the MTP-PE adjuvants.

TABLE 12

Test of MTP-PE-LO-MF #1 as an Adjuvant for HIV Protein env2 and gp120 in Baboons

| Group | Animal Number | Adjuvant | Antigen | Virus ELISA Titer After 2 Immunizations | Neutralizing Antibody Titer |
|---|---|---|---|---|---|
| 1 | 2947 | MTP/IFA | gp120 (55 mg) | <100 | <10 |
| | 2948 | (350 mgMTP-PE) | gp120 (55 mg) | <100 | <10 |
| | 2949 | " | gp120 (55 mg) | 3000 | <10 |
| 2 | 2550 | MTP-PE/IFA | env2 (25 mg) | 400 | <10 |
| | 2451 | (250 mg MTP-PE) | env2 (25 mg) | 34,500 | 30 |
| | 2952 | " | env2 (25 mg) | 142,300 | 200 |
| 3 | 2953 | MTP-PE-LO-MF #1[a] | gp120 (55 mg) | 51,000 | 200 |
| | 2957 | " | gp120 (55 mg) | 43,000 | 35 |
| | 2595 | " | gp120 (55 mg) | 800 | 50 |
| 4 | 2956 | MTP-PE-LO-MF #1 | env2 (25 mg) | 600 | <10 |
| | 2957 | " | env2 (25 mg) | 14,400 | 35 |
| | 2958 | " | env2 (25 mg) | 87,400 | >250 |
| 5 | 2964 | Alum[b] | gp120 (55 mg) | 56,000 | 150 |
| | 2965 | " | gp120 (55 mg) | 100 | <10 |
| 6 | 2966 | Alum | env2 (25 mg) | 4900 | 80 |
| | | " | env2 (25 mg) | 700 | <10 |

[a]MTP-PE-LO-MF #1 - 2% squalene, 500 mg/ml MTP-PE, 0 Tween 80, H₂O. Oil droplet size –0.17 microns.
[b]Alum antigen bound to 0.8 mg/ml aluminum hydroxide.

EXAMPLE 4

Additional Adjuvant/antigen Formulations

In addition to the detailed examples set forth above, a number of other antigens have been prepared in vaccine formulations containing adjuvant compositions of the invention. These include antigens from pathogens responsible for influenza and malaria, as well as antigens associated with HIV and HSV other than those described in previous examples. Antigens from cytomegalovirus (CMV) and hepatitis C virus (HCV) are also described, as these antigens can be used in the same adjuvant formulations described for the other indicated antigens.

Antigens

Influenza antigens suitable for use in vaccine preparations are commercially available. Antigens used in the following examples are "FLUOGEN", manufactured by Parke-Davis; Duphar, manufactured by Duphar B. V.; and influenza vaccine batch A41, manufactured by Instituto Vaccinogeno Pozzi.

Malaria antigens suitable for use in vaccine preparations are described in U.S. patent application Ser. No. 336,288, filed Apr. 11, 1989, and in U.S. Pat. No. 4,826,957, issued May 2, 1989.

Additional HIV antigens suitable for use in vaccine preparations are described in U.S. application Ser. No. 490,858, filed Mar. 9, 1990. Also see published European application number 181150 (May 14, 1986) for additional HIV antigens.

Additional HSV antigens suitable for use in vaccine preparations are described in PCT WO85/04587, published Oct. 24, 1985, and PCT WO88/02634, published Apr. 21, 1988. Mixtures of gB and gD antigens, which are truncated surface antigens lacking the anchor regions, are particularly preferred.

Cytomegalovirus antigens suitable for use in vaccine preparations are described in U.S. Pat. No. 4,689,225, issued Aug. 25, 1987, and in PCT application PCT/US89/00323, published Aug. 10, 1989 under International Publication Number WO 89/07143. Also see U.S. application Ser. No. 367,363, filed Jun. 16, 1989.

Hepatitis C antigens suitable for use in vaccine preparations are described in PCT/US88/04125, published European application number 318216 (May 13, 1989), published Japanese application number 1-500565 (filed Nov. 18, 1988), and Canadian application 583,561. A different set of HCV antigens is described in European patent application 90/302866.0, filed Mar. 16, 1990. Also see U.S. application Ser. No. 456,637, filed Dec. 21, 1989, and PCT/US90/01348.

It should be noted that published versions of the various unpublished application numbers listed above can be obtained from an indexing service, such as World Patent Index, as well as a listing of corresponding applications in other countries.

Adjuvant Formulations and Preparation Techniques

The following summaries describe adjuvant formulations and how they are prepared as well as vaccine compositions prepared using the adjuvants and various antigenic substances. In some cases summaries of vaccination studies are provided, but without the detail of the examples above, since the vaccination studies set forth above already provide sufficient guidance for use of the vaccine compositions.

Influenza

In a series of experiments, hamsters were immunized with a commercial influenza vaccine from Instituto Vaccinogeno Pozzi. This vaccine consists of purified HA from two A strains (A/Leningrad/360/86 and A/Singapore/6/86) and one B strain (B/Ann Arbor/1/86). The vaccine was tested alone, with an MTP-PE/LO emulsion made with a Kirkland emulsifier (Fluoromed Pharmaceutical Inc., La Mesa, Calif.) and with an MTP-PE/MF emulsion made in a microfluidizer (model 110Y, Microfluidics, Newton, Mass.). The first two are comparative compositions, while the "MF" composition is a composition of the invention. MTP-PE/MF stands for "MTP-PE Microfluidizer" emulsion and contains 4% squalene and 1.0 mg/ml MTP-PE emulsified with the Microfluidizer. The MTP-PE Kirkland emulsion contained 4% squalene, 0.5 mg/ml MTP-PE, and 0.008% Tween 80 emulsified with the Kirkland emulsifier. Animals received three immunizations containing 8.3 $\mu$g of each HA antigen. MTP-PE was used at 50 $\mu$g per dose in both formulations. ELISA titers were determined against the immunizing antigens after each immunization and HAI titers were determined after the second immunization. ELISA titers were increased substantially by both of the adjuvant formulations tested.

In other experiments, hamsters were immunized with either the commercially available Parke-Davis "FLUOGEN" vaccine (HA A/Shanghai/11/87, A/Taiwan/1/86 and B/Yamagata/16/88) or the commercially available Duphar influenza vaccine (HA A/Sechuan/2/87, A/Singapore/6/86 and B/Beijing/1/87) alone or with the MF69 adjuvant formulation (MF69 is 5% squalene, 0.2% Tween 80, 0.8%, Span 85, and 400 $\mu$g/ml MTP-PE, emulsified in the Microfluidizer). Equal volumes of vaccine were mixed with the MF69 adjuvant. Animals received three immunizations of 11.25 ig of the Parke-Davis vaccine or 7.5 $\mu$g of the Duphar vaccine at three week intervals. Animals receiving the MF69 adjuvant received 50 $\mu$g doses of MTP-PE. The animals receiving Duphar plus MF69 showed significantly higher anti-HA titers than Duphar alone after one and two immunizations (mean titers 80-fold higher than vaccine alone after one immunization and 170-fold higher than after two immunizations). The MF69 adjuvant showed good stimulation of antibody response to the Parke-Davis vaccine, generating mean titers of 2951, 14,927 and 12,878 after one, two or three immunizations. This represents titers 82, 29 and 10-fold higher than vaccine alone after one, two or three immunizations, respectively. For both vaccines, peak antibody titers were seen after two immunizations with MF 69.

In further experiments, the immunogenicity of two commercial influenza vaccines, Parke-Davis "FLUOGEN" and Duphar subunit influenza, were compared with no adjuvant and with several MTP-PE containing adjuvant formulations in goats. The animals were immunized intramuscularly with 0.5 ml of each vaccine mixed with either 0.5 ml of PBS or 0.5 ml of MTP-PE adjuvant formulations. Three adjuvant formulations were compared: 200 $\mu$g of MTP-PE dissolved in PBS, and 200 $\mu$g of MTP-PE in two different microfluidized emulsions, referred to as Gaulin 1/4 and MF40/4 emulsions. Gaulin 1/4 consists of 1.6% squalene and 400 $\mu$g/ml MTP-PE emulsified in the Goblin homogenizer (APV Gaulin, Everett, Mass.). MTP-PE/MF-40/4 consists of 1.6% squalene, 400 $\mu$g/ml MTP-PE, 0.154% Tween 85, and 0.166% Span 85 emulsified in the Microfluidizer (Model 110Y, Microfluidics, Newton, Mass.). Animals received 0.5 ml of vaccine mixed with either 0.5 ml of PBS or 0.5 ml of the indicated adjuvant formulation to generate a 1.0 ml injection volume. As with the hamsters, the goats receiving the influenza vaccines combined with the adjuvant emulsions showed much higher antibody titers than goats receiving vaccine alone. This is especially pronounced early in the immunization schedule. After one immunization the Gaulin 1/4 emulsion generated anti-HA titers greater than 30-fold higher than the Parke-Davis vaccine alone. The MTP-PE/MF-40 emulsion generated anti-HA titers that were greater than 130-fold higher than Parke-Davis vaccine alone and 60-fold higher than Duphar vaccine alone. MTP-PE in PBS showed no stimulation of antibody titer after one immunization. After two immunizations, similar increases in antibody titers with the emulsions were seen. The early stimulation of anti-HA titers seen with the adjuvant emulsions is especially significant since influenza vaccines are generally given as one dose vaccines to adults and two dose vaccines to infants. Thus, as in hamsters, the MTP-PE-emulsions show large increases in the immune response to influenza vaccines.

In another experiment, the Duphar vaccine was compared alone and with adjuvant formulation MF69. The Parke-Davis vaccine was compared alone and with MF101, MF69, MF-68+MTP-PE, and the Ribi Adjuvant system made in the Gaulen homogenizer (micro-fluidizer). MF-101 consists of 1.6% squalene and 400 ug/ml MTP-PE, emulsified in the Microfluidizer. MF-68 consists of 5% squalene, 0.8% Span 85, and 0.2% Tween 80, emulsified in the Microfluidizer. MF-68+MTP consists of MF-68 to which was added 400 ug/ml MTP-PE per ml post emulsification. Ribi-MF consists of 2% squalene, 0.4% Tween 20, 250 ug/ml monophosphoryl lipid A, 250 ug/ml Trehalose dimycolate, and 250 ug/ml cell wall skeleton (Ribi Immunochem, Hamilton Mont.), emulsified in the Gaulin homogenizer. All adjuvants were used at a dose of 0.5 ml per injection with equal volumes of vaccine (antigen). MF69 significantly increased the ELISA titer to the Duphar vaccine. All of the adjuvants tested also significantly increased the immunogenicity of the Parke-Davis vaccine as measured by both ELISA titer and hemagglutination titer.

In a further experiment, MF69 and MF59 formulations (differing only in the Tween 80:Span 85 ratio; see descriptions above) were compared as adjuvants with the Parke-Davis influenza vaccine in goats. The animals were immunized once with one-half of the human vaccine dose (7.5 $\mu$g each of the three HA components) combined with the adjuvant formulations. MTP-PE was used at a dose of 100 $\mu$g in the formulations. As expected, the two formulations give very similar titers with the MF69 showing a mean titer of 926 and the MF59 showing a mean titer of 821.

Malaria

A vaccination study has been initiated using MF59 (described above) as adjuvant. A mixture of commercially available antigens from the sporozoite, merozoite, and erythrocytic stages of the disease was used: Falc. 2.3 circumsporozoite antigen, HP 195 merozoite antigen, and SERA 1 red blood stage antigen. Vaccine compositions are prepared as described above, namely mixing equal volumes of the previously prepared MF59 adjuvant and the antigen composition.

HIV

An immunization experiment was carried out to compare production of neutralizing antibodies by a number of different gp120 antigens. Details of preparation of the antigens are set forth in U.S. application Ser. No. 490,858, filed Mar. 9, 1990. One antigen was a gp120 analog (env 2–3) prepared in yeast, which is denatured and non-glycosylated. Another antigen was glycosylated gp120 retaining its natural configuration. Both gp120 materials were derived from the same gene source, HIV-1 SF-2 isolate. Antibody production was measured in baboons. Initial studies using oil-containing adjuvants with particle sizes larger than 1 micron produced titers less than those produced using conventional alum adjuvants. However, later studies with submicron particle adjuvants produced antibody titers at least 10-fold higher than with alum. The initial submicron composition contained 2% squalene and 0.500 mg/ml MTP-PE in water and had oil droplets averaging about 0.17 microns in diameter. Vaccine compositions using MF59 (described above) or MF58 (MF59 but with MTP-PE added exogenously) as an adjuvant in baboons have proven even more effective in stimulating antibody production than the initial submicron composition used. MF59 was used at a 1:2 dilution at a rate of 0.100 mg MTP-PE.

Herpes Simplex Virus

In addition to the gD2 experiments described above, additional experiments have been carried out using MF59 and various amounts of MTP-PE and antigens. Satisfactory antibody tiers have been obtained using from 0.003 to 0.250 mg gD2 with MF59 adjuvant and 0.050 mg MTP-PE in guinea pigs (intramuscular administration) and using from 0.010 to 0.100 mg gD2 with MF59 and 0.100 mg MTP-PE.

Cytomegalovirus

Vaccine formulations can be prepared by mixing from 0.001 to 0.250 mg of CMV antigens in 0.5 ml physiological saline with 0.5 ml MF59 adjuvant containing 0.050 mg MTP-PE. MF69, MF101, and other submicron particle adjuvants can be used in the same manner.

Hepatitis C Virus

Vaccine formulations can be prepared by mixing from 0.001 to 0.250 mg of HCV antigens in 0.5 ml physiological saline with 0.5 ml MF59 adjuvant containing 0.050 mg MTP-PE. MF69, MF101, and other submicron particle adjuvants can be used in the same manner.

All publications and patent applications cited herein are incorporated by reference in the location where cited to the same extent as if each individual publication or patent application had been individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A composition comprising:
   (1) an adjuvant composition consisting essentially of: (a) a metabolizable oil, wherein the oil is present in an amount of 0.5% to 15% of the total volume and (b) an emulsifying agent, wherein the emulsifying agent is 0.01% to 2.5% by weight (w/w), and wherein said oil and said emulsifying agent are present in the form of an oil-in-water emulsion having oil droplets substantially all of which are about 100 nm to less than 500 nm in diameter and wherein said composition exists in the absence of any polyoxypropylene-polyoxyethylene block copolymer; and
   (2) an antigenic substance, wherein said antigenic substance is not present in the internal phase of the adjuvant composition and further wherein said adjuvant composition is capable of increasing the immune response to the antigenic substance.

2. The composition of claim 1 wherein the antigenic substance is from a virus.

3. The composition of claim 2 wherein the antigenic substance comprises a viral subunit.

4. The composition of claim 2 wherein the virus is selected from the group consisting of hepatitis C virus (HCV), herpes simplex virus (HSV), human immunodeficiency virus (HIV), cytomegalovirus (CMV), influenza virus (flu), poliovirus, and rabies virus.

5. The composition of claim 4 wherein the antigenic substance is from herpes simplex virus (HSV).

6. The composition of claim 5 wherein the antigenic substance comprises HSV glycoprotein gD.

7. The composition of claim 4 wherein the antigenic substance is from human immunodeficiency virus (HIV).

8. The composition of claim 7 wherein the antigenic substance comprises HIV glycoprotein gp120.

9. The composition of claim 2 further comprising one or more additional antigenic substances.

10. The composition of claim 1 wherein the antigenic substance is from a bacterium.

11. The composition of claim 10 wherein the bacterium is selected from the group consisting of cholera, diphtheria, tetanus, and pertussis.

12. The composition of claim 10 further comprising one or more additional antigenic substances.

13. The composition of claim 1 wherein the antigenic substance is from a parasite.

14. The vaccine composition of claim 13 wherein the parasite comprises a malaria parasite.

15. The composition of claim 1 wherein the antigenic substance is used to immunize against meningitis.

16. The composition of claim 1 further comprising one or more additional antigenic substances.

17. The composition of claim 1 wherein the antigenic substance is selected from the group consisting of a protein, protein-polysaccharide, protein-lipopolysaccharide, polysaccharide, and lipopolysaccharide.

18. The composition of claim 1 wherein the antigenic substance comprises a hapten.

19. The composition of claim 1 further comprising an additional immunostimulatory agent.

20. The composition of claim 19 wherein the additional stimulatory agent is a muramyl peptide.

21. The composition of claim 1 wherein the oil is present in an amount of 1% to 12% of the total volume and the emulsifying agent is 0.05% to 1% by weight (w/w).

22. The composition of claim 1 wherein the oil is present in an amount of 1% to 4% of the total volume.

23. The composition of claim 1 wherein the emulsifying agent is 0.01% to 0.05% by weight (w/w).

24. The composition of claim 1, wherein said oil is an animal oil.

25. The composition of claim 1, wherein said oil is an unsaturated hydrocarbon.

26. The composition of claim 1, wherein said oil is a terpenoid.

27. The composition of claim 1, wherein said oil is a vegetable oil.

28. The composition of claim 1, wherein said emulsifying agent comprises a non-ionic detergent.

29. The composition of claim 1, wherein said emulsifying agent comprises a polyoxyethylene sorbitan mono-, di-, or triester or a sorbitan mono-, di-, or triester.

30. The composition of claim 29, wherein said composition comprises 0.02 to 2.5% by weight of said emulsifying agent.

31. The composition of claim 1, wherein said emulsifying agent comprises a polyoxyethylene sorbitan mono-, di-, or triester and a sorbitan mono-, di-, or triester.

32. The composition of claim 31, wherein said oil is squalene.

33. A process for producing a composition comprising the steps of:
  (a) providing an adjuvant composition, wherein said adjuvant composition consists essentially of: (i) a metabolizable oil, wherein the oil is present in an amount of 0.5% to 15% of the total volume and (ii) an emulsifying agent, wherein the emulsifying agent is 0.01% to 2.5% by weight (w/w), and wherein said oil and said emulsifying agent are present in the form of an oil-in-water emulsion having oil droplets substantially all of which are about 100 nm to less than 500 nm in diameter and wherein said composition exists in the absence of any polyoxypropylene-polyoxyethylene block copolymer; and
  (b) adding an antigenic substance to said adjuvant composition, wherein said antigenic substance is not present in the internal phases of the adjuvant composition and further wherein said adjuvant composition is capable of increasing the immune response to the antigenic substance.

34. The process of claim 33, further comprising adding an additional immunostimulatory agent to said adjuvant composition.

35. The process of claim 34, wherein the additional stimulatory agent is a muramyl peptide.

36. The process of claim 33, wherein the oil is present in an amount of 1% to 12% of the total volume and the emulsifying agent is 0.05% to 1% by weight (w/w).

37. The process of claim 33, wherein the oil is present in an amount of 1% to 4% of the total volume.

38. The process of claim 33, wherein the emulsifying agent is 0.01% to 0.05% by weight (w/w).

39. A composition produced according to the process of claim 33.

40. The process of claim 33, wherein said emulsifying agent comprises a polyoxyethylene sorbitan mono-, di-, or triester and a sorbitan mono-, di-, or triester.

41. The process of claim 40, wherein said oil is squalene.

42. A composition comprising:
  (1) an adjuvant composition consisting essentially of: (a) 5% by volume of squalene; and (b) one or more emulsifying agents selected from the group consisting of a polyoxyethylenesorbitan ester and a sorbitan ester, wherein the total amount of emulsifying agent(s) present is 1% by weight (w/w); wherein said squalene and said emulsifying agent(s) are present in the form of an oil-in-water emulsion having oil droplets substantially all of which are about 100 nm to less than 500 nm in diameter and wherein said composition exists in the absence of any polyoxypropylene-polyoxyethylene block copolymer; and
  (2) an antigenic substance, wherein said antigenic substance is not present in the internal phase of the adjuvant composition and further wherein said adjuvant composition is capable of increasing the immune response to the antigenic substance.

43. The composition of claim 42, wherein the one or more emulsifying agents are a polyoxyethylenesorbitan ester and a sorbitan ester and the total amount of a polyoxyethylenesorbitan ester and a sorbitan ester present is 1% by weight (w/w).

44. A process for producing a composition comprising the steps of:
  (a) providing an adjuvant composition, wherein said adjuvant composition consists essentially of: (i) 5% by volume of squalene; and (ii) one or more emulsifying agents selected from the group consisting of a polyoxyethylenesorbitan ester and a sorbitan ester, wherein the total amount of emulsifying agent(s) present is 1% by weight (w/w); wherein said squalene and said emulsifying agent(s) are present in the form of an oil-in-water emulsion having oil droplets substantially all of which are about 100 nm to less than 500 nm in diameter and wherein said composition exists in the absence of any polyoxypropylene-polyoxyethylene block copolymer; and
  (b) adding an antigenic substance to said adjuvant composition, wherein said antigenic substance is not present in the internal phase of the adjuvant composition and further wherein said adjuvant composition is capable of increasing the immune response to the antigenic substance.

45. The process of claim 44, wherein the one or more emulsifying agents are a polyoxyethylenesorbitan ester and a sorbitan ester and the total amount of a polyoxyethylenesorbitan ester and a sorbitan ester present is 1% by weight (w/w).

46. A composition comprising:
  (1) an adjuvant composition comprising: (a) 5% by volume of squalene; and (b) one or more emulsifying agents selected from the group consisting of polyoxyethylenesorbitan monooleate and sorbitan trioleate, wherein the total amount of emulsifying agent(s) present is 1% by weight (w/w); wherein said squalene and said emulsifying agent(s) are present in the form of an oil-in-water emulsion having oil droplets substantially all of which are about 100 nm to less than 500 nm in diameter and wherein said composition exists in the absence of any polyoxypropylene-polyoxyethylene block copolymer; and
  (2) an antigenic substance, wherein said antigenic substance is not present in the internal phase of the adjuvant composition and further wherein said adjuvant composition is capable of increasing the immune response to the antigenic substance.

47. The composition of claim 46, wherein the one or more emulsifying agents are polyoxyethylenesorbitan monooleate and sorbitan trioleate and the total amount of polyoxyethylenesorbitan monooleate and sorbitan trioleate present is 1% by weight (w/w).

48. A process for producing a composition comprising the steps of:
  (a) providing an adjuvant composition, wherein said adjuvant composition comprises: (i) 5% by volume of squalene; and (ii) one or more emulsifying agents selected from the group consisting of polyoxyethylenesorbitan monooleate and sorbitan trioleate, wherein the total amount of emulsifying agent(s) present is 1% by weight (w/w); wherein said squalene and said emulsifying agent(s) are present in the form of an oil-in-water emulsion having oil droplets substantially all of which are about 100 nm to less than 500 nm in diameter and wherein said composition exists in the absence of any polyoxypropylene-polyoxyethylene block copolymer; and (b) adding an antigenic substance to said adjuvant composition, wherein said antigenic substance is not present in the internal phase of the adjuvant composition and further wherein said adjuvant composition is capable of increasing the immune response to the antigenic substance.

49. The process of claim 48, wherein the one or more emulsifying agents are polyoxyethylenesorbitan monooleate and sorbitan trioleate and the total amount of polyoxyethylenesorbitan monooleate and sorbitan trioleate present is 1% by weight (w/w).

* * * * *